United States Patent
Kerr et al.

(10) Patent No.: US 10,702,538 B2
(45) Date of Patent: Jul. 7, 2020

(54) SHIP INHIBITION TO INDUCE ACTIVATION OF NATURAL KILLER CELLS

(71) Applicant: THE RESEARCH FOUNDATION FOR THE STATE UNIVERSITY OF NEW YORK, Syracuse, NY (US)

(72) Inventors: William Kerr, Syracuse, NY (US); Matthew Gumbleton, Syracuse, NY (US)

(73) Assignee: THE RESEARCH FOUNDATION FOR THE STATE UNIVERSITY OF NEW YORK, Syracuse, NY (US)

(*) Notice: Subject to any disclaimer, the term of this patent is extended or adjusted under 35 U.S.C. 154(b) by 0 days.

(21) Appl. No.: 15/319,326

(22) PCT Filed: Jun. 17, 2015

(86) PCT No.: PCT/US2015/036246
§ 371 (c)(1),
(2) Date: Dec. 15, 2016

(87) PCT Pub. No.: WO2015/195812
PCT Pub. Date: Dec. 23, 2015

(65) Prior Publication Data
US 2017/0151262 A1    Jun. 1, 2017

Related U.S. Application Data

(60) Provisional application No. 62/013,511, filed on Jun. 17, 2014.

(51) Int. Cl.
| | | |
|---|---|---|
| A61K 31/56 | (2006.01) | |
| A61K 9/19 | (2006.01) | |
| A61K 9/00 | (2006.01) | |
| A61K 31/4045 | (2006.01) | |
| A61K 31/565 | (2006.01) | |
| A61K 31/435 | (2006.01) | |
| A61K 31/568 | (2006.01) | |
| C12N 15/113 | (2010.01) | |
| A61K 31/575 | (2006.01) | |

(52) U.S. Cl.
CPC ........... *A61K 31/56* (2013.01); *A61K 9/0019* (2013.01); *A61K 31/4045* (2013.01); *A61K 31/435* (2013.01); *A61K 31/565* (2013.01); *A61K 31/568* (2013.01); *A61K 31/575* (2013.01); *C12N 15/1137* (2013.01); *C12N 2310/14* (2013.01); *C12N 2310/141* (2013.01)

(58) Field of Classification Search
None
See application file for complete search history.

(56) References Cited

U.S. PATENT DOCUMENTS

| | | | |
|---|---|---|---|
| 5,030,449 | A | 7/1991 | Berzofsky et al. |
| 5,710,143 | A | 1/1998 | Suzuki et al. |
| 9,447,139 | B2 | 9/2016 | Kerr |
| 2011/0052546 | A1 | 3/2011 | Desponts et al. |
| 2012/0178725 | A1 | 7/2012 | Kerr |
| 2013/0102577 | A1* | 4/2013 | Kerr ..................... A61K 31/56 514/178 |
| 2016/0129017 | A1 | 5/2016 | Kerr |
| 2017/0051006 | A1 | 2/2017 | Kerr |

FOREIGN PATENT DOCUMENTS

| | | |
|---|---|---|
| BE | 702699 | 1/1968 |
| CZ | 126738 | 5/1968 |
| EP | 133995 | 4/1992 |
| GB | 900572 | 7/1962 |
| WO | WO1989001973 | 3/1989 |
| WO | WO2004032880 | 4/2004 |
| WO | WO 2008/022468 A1 | 2/2008 |
| WO | WO2008068037 | 6/2008 |
| WO | WO 2008/124815 A1 | 10/2008 |
| WO | WO2009032321 | 3/2009 |
| WO | WO2010045199 | 4/2010 |
| WO | WO2011069118 | 6/2011 |
| WO | WO2011127465 | 10/2011 |
| WO | WO2014089029 | 6/2014 |
| WO | WO2015003003 | 1/2015 |

OTHER PUBLICATIONS

Balch, A Novel Therapeutic Approach in Breast and Hematopoietic Cancers: Inhibition of SH2-Domain Containing Inositol 5' Phosphatase (SHIP), Syracuse University SURFACE, May 1, 2013.*
Ahmad et al. (2009) "Synthesis of facial amphiphile 3,7-diamino-5.alpha.-cholestane derivatives as a molecular receptor," Bulletin of the Korean Chemical Society. 30(9):2101-2106.
Annis et al. (Sep. 1, 2009) "Inhibitors of the Lipid Phosphatase SHIP2 Discovered by High Throughput Affinity Selection-Mass Spectrometry Screening of Combinatorial Libraries," Combinatorial Chemistry and High Throughput Screening. 12(8):760-771.
Bai et al. (2010) "s-SHIP promoter expression marks activated stem cells in developing mouse mammary tissue," Genes Dev. 24:1882-1892.
Bar-Yehuda et al. (Dec. 2002) "Agonists to the A3 adenosine receptor induce G-CSF production via NF-κb activation," Experimental Hematology. 30(12):1390-1398.
Beerman et al. (Mar. 23, 2010) "Functionally distinct hematopoietic stem cells modulate hematopoietic lineage potential during aging by a mechanism of clonal expansion," Proc Natl Acad Sci. 107(12):5465-5470.
Blunt et al. (Aug. 1, 2012) "Targeting PI3K 1-15 isoforms and SHIP in the immune system: new therapeutics for inflammation and leukemia," Current Opinion in Pharmacology. 12(4):444-451.
Brooks et al. (Apr. 1, 2010) "SHIP1 inhibition increases immunoregulatory capacity and triggers apoptosis of hematopoietic cancer cells," J Immunol. 184(7):3582-3589.

(Continued)

*Primary Examiner* — Jared Barsky
(74) *Attorney, Agent, or Firm* — Lathrop GPM LLP

(57) ABSTRACT

The present invention relates to the use of SHIP1 inhibitors and pan-SHIP1/2 inhibitors in various methods, including, without limitation, a method of inhibiting SHIP to induce broad activation of natural killer (NK) cells to treat various diseases.

18 Claims, 7 Drawing Sheets

(56) References Cited

OTHER PUBLICATIONS

Brooks et al. (Nov. 17, 2014) "Coordinate Expansion of Murine Hematopoietic and Mesenchymal Stem Cell Compartments by SHIPi," Stem Cells. Supplemental Information and 33:848-858.
Conde et al. (Jul. 17, 2012) "The inositol phosphatase SHIP-I inhibits NOD2-induced NF-kappaB activation by disturbing the interaction of XIAP with RIP2," PLoS One. 7:e41005.
Cowell et al. (Jan. 1, 1974) "Bromo, Chloro-, and Amino Derivates of 5alpha-androstane and 5alpha-Oestrane," Journal of the Chemical Society, Perkin Transactions, Chemical Society. 1(13):1505-1513.
Desponts et al. (2006) "SHIP deficiency enhances HSC proliferation and survival but compromises homing and repopluation,"Blood. 107:4338-4345.
Douillard et al. (2014) "Final results from PRIME: randomized phase III study of panitumumab with FOLFOX4 for first line treatment of metastatic colorectal cancer," Ann Oneal. 25(7):1346-1355.
Extended European Search Report corresponding to European Patent Application No. 11766857.4, dated Jan. 17, 2014.
Fernandes et al. (Feb. 13, 2015) "SHIPi Enhances Autologous and Allogeneic Hematopoietic Stem Cell Transplantation," EBioMedicine. 2:205-213.
Francisco et al. (Jan. 1, 1990) "Aminoselenenylation of Alkenes: Syntheses of p-Phenylseleno Carbamates and p-Phenylseleno Cyanamides," Journal of the Chemical Society. 9:2417-2427.
Fuhler et al. (Oct. 19, 2011) "Therapeutic Potential of SH2 Domain-Containing Inositol-5'-Phosphatase 1 (SHIP1) and SHIP2 Inhibition in Cancer," Molecular Medicine. 18:65-75.
Fujita et al. (2004) "Runx2 induces osteoblast and chondrocyte differentiation and enhances their migration by coupling with PBK-Akt signaling," J Cell Biol. 166:85-95.
Fukuda (2001) "Development of regenerative cardiomyocytes from mesenchymal stem cells for cardiovascular tissue engineering," ArtifOrgans. 25(3):187-193.
Geest et al. (2009) "MAPK signaling pathways in the regulation of hematopoiesis," J Leukoc Biol. 86:237-250.
Ghansah et al. (2004) "Expansion of myeloid suppressor cells in SHIP deficient mice represses allogeneic T cell responses," J Immunol. 173:7324-7330.
Gibbs et al. (2011) "Single-cell phospho-specific flow cytometric analysis demonstrates biochemical and functional heterogeneity in human hematopoietic stem and progenitor compartments," Blood. 117:4226-4233.
Grothey et al. (2013) "Regorafenib monotherapy for previously treated metastatic colorectal cancer (CORRECT): an international, multicentre, randomised, placebo-controlled, phase 3 trial," Lancet. 381(9863):303-312.
Han et al. (2012) "Concordant KRAS Mutations in Primary and Metastatic Colorectal Cancer Tissue Specimens: A Meta-Analysis and Systematic Review," Cancer Investigation. 30(10):741-747.
Harwood et al. (Jul. 19, 1998) "The synthesis of 3.alpha.-/3.beta.-cholesteryl and cholestanyl esters and ethers—an assessment of their mesogenicity," Gordon and Breach Publishers. 332:485-495.
Hazen et al. (2009) "SHIP is required for a functional hematopoietic stem cell niche," Blood. 113:2924-2933.
Helgason et al. (1998) "Targeted disruption of SHIP leads to hemopoietic perturbations, lung pathology, and a shortened life span," Genes & Development. 12:1610-1620.
Helgason et al. (2003) "Homeostasis and regeneration of the hematopoietic stem cell pool is altered in SHIP-deficient mice," Blood. 102:3541-3547.
Hungria et al. (Oct. 22, 2003) "Metabolism of a Cholesterol-Rich Microemulsion (IDE) in Patients with Multiple Myeloma and a Preliminary Clinical Study of LDE as a Drug Vehicle for the Treatment of the Disease," Cancer Chemotherrn Pharmacol. 51-60.
Hunter et al. (1998) "Phosphatidylinositol 3'-kinase and SH2-containing inositol phosphatase (SHIP) are recruited by distinct positive and negative growth-regulatory domains in the granulocyte colony-stimulating factor receptor," Journal of Immunology. 160:4979-4987.
Hunter et al. (2004) "Loss of SHIP and CIS recruitment to the granulocyte colony-stimulating factor receptor contribute to hyperproliferative responses in severe congenital neutropenia/acute myelogenous leukemia," J Immunol. 173:5036-5045.
International Search Report with Written Opinion corresponding to International Patent Application No. PCT/US2011/031930, dated Dec. 27, 2011.
Iyer et al. (Mar. 2013) "Role of SHIP1 in bone biology," Ann NY Acad Sci. 1280:11-14.
Iyer et al. (May 24, 2014) "SHIP1 Regulates MSC Numbers and Their Osteolineage Commitment by Limiting Induction of the PI3K/Akt/β-Catenin/Id2 Axis," Stem Cells Dev. 23(19):2336-2351.
Jang et al. (Apr. 30, 2009) "Synthesis of 9-Anthryl Ethers from trans-9, 10-Dihydro-9, 10-dimethoxy-anthracene by Acid-Catalyzed Transetherification," Synthesis. 10:1703-1707.
Kerr (2008) "A role for SHIP in stem cell biology and transplantation," Curr Stem Cell Res Ther. 3:99-106.
Kerr et al. (2010) "Ship deficiency causes Crohn's disease-like ileitis," Gut. 60:177-188.
Kerr (2011) "Inhibitor and activator: dual functions for SHIP in immunity and cancer," Ann NY Acad Sci. 1217:1-17.
Li et al. (Jan. 5, 1999) "Short Syntheses of Triamine Derivatives of Cholic Acid," Tetrahedron Letters. 40:1861-1864.
Li et al. (Apr. 2012) "An essential role for the Id1/PI3K/Akt/NFkB/survivin signalling pathway in promoting the proliferation of endothelial progenitor cells in vitro," Mol Cell Biochem. 363:135-145.
Lieschke et al. (1992) "Granulocyte colony-stimulating factor and granulocytemacrophage colony-stimulating factor," n. Engl J Med. 327:99-106.
Lievre et al. (2006) "KRAS mutation status is predictive of response to cetuximab therapy in colorectal cancer," Cancer Res. 66(8):3992-3995.
Link (2000) "Mechanisms of granulocyte colony-stimulating factor-induced hematopoietic progenitor-cell mobilization," Semin Hematol. 37:25-32.
Liu et al. (Mar. 15, 2005) "Dehydroepiandrosterone Can Inhibit the Proliferation of Myeloma Cells and the Interleukin-6 Production of Bone Marrow Mononuclear Cells from Patients with Myeloma," Cancer Research. 65:2269-2276.
Luyendyk et al. (2008) "Genetic analysis of the role of the PI3KAkt pathway in lipopolysaccharide-induced cytokine and tissue factor gene expression in monocytes/macrophages," J Immunol. 180:4218-4226.
Manhas et al. (Jan. 1, 1975) "Steroids. Part X. A Convenient Synthesis of Alkyl Aryl Ethers," Journal of the Chemical Society, Perkin Transactions 1: Organic and Bio-Organic Chemistry. 1(5):461-463.
Mathis (Jun. 1, 2013) "Immunological Goings-on in 1-15 Visceral Adipose Tissue," Cell Metabolism. 17(6):851-859.
Maxwell et al. (2014) "SHIP-I deficiency in the myeloid compartment is insufficient to induce myeloid expansion or chronic inflammation," Genes Immun. 15:233-240.
Medline Plus, Jul. 22, 2008, pp. 1-4, <http://www.nlm.nih.gov/medlineplus/fungalinfections.html>.
Mendez-Ferrer et al. (Aug. 12, 2010) "Mesenchymal and haematopoietic stem cells form a unique bone marrow niche," Nature. 466(7308):829-834.
Molineux et al. (1990) "A comparison of hematopoiesis in normal and splenectomized mice treated with granulocyte colony-stimulating factor," Blood. 75:563-569.
Morikawa et al. (2009) "Prospective identification, isolation, and systemic transplantation of multipotent mesenchymal stem cells in murine bone marrow," J Exp Med. 206:2483-2496.
Morrison et al. (1997) "Cyclophospharnide/Granulocyte colony stimulating factor induces hematopoietic stem cells to proliferate prior to mobilization," Proc Natl Acad Sci. 94:1908-1913.
Muller-Sieburg et al. (2004) "Myeloid-biased hematopoietic stem cells have extensive self-renewal capacity but generate diminished lymphoid progeny with impaired IL-7 responsiveness," Blood. 103:4111-4118.

(56) References Cited

OTHER PUBLICATIONS

Nikolaropoulos et al. (Mar. 13, 1990) "Formation of Acetamido-Aza Steroids," J. Heterocyclic Chem. 27(7):1997-1999.
Nioche et al. (1988) "Production of granulocyte colony-stimulating factor (G-CSF) by human cells: T lymphocyte-dependent and T lymphocyte-independent release of G-CSF by blood monocytes," Eur J Immunol. 18:1021-1026.
O'Neill et al. (1997) "NF-kappa B: a crucial transcription factor for glial and neuronal cell function," Trends Neurosci. 20:252-258.
Osawa et al. (1996) "Long-term lymphohematopoietic reconstitution by a single CD34-low/negative hematopoietic stem cell," Science. 273:242-245.
Perry et al. (Sep. 2, 2011) "Cooperation between both Wnt/{beta}-catenin and PTEN/PBK/Akt signaling promotes primitive hematopoietic stem cell self-renewal and expansion," Genes Dev. 25:1928-1942.
Phillipps et al. (1983) "A New Series of Steroidal Antidysrhythmic Agents," J Steroid Biochem. 19(1):759-765.
Pinho et al. (Jun. 17, 2013) "PDGFRalpha and CD51 mark human nestin+ sphere-forming mesenchymal stem cells capable of hematopoietic progenitor cell expansion," J Exp Med. 210:1351-1367.
Polak et al. (2012) "The PI3K/PKB signaling module as key regulator of hematopoiesis: implications for therapeutic strategies in leukemia," Blood. 119:911-923.
Ponsold et al. (Jan. 1, 1966) "Dartsellung and Ringoffnungsreaktionen der epirneren 2.3-Imino-cholestane," Chemische Berichte. 99(5):1502-1508.
Seshacharyulu et al. (2012) "Targeting the EGFR signaling pathway in cancer therapy," Expert Opinion on Therapeutic Targets. 15-31.
Shojaei et al. (2007) "Bv8 regulates myeloid-cell-dependent tumour angiogenesis," Nature. 450:825-831.
Siegel et al. (2014) "Colorectal cancer statistics," CA Cancer J Clin. 64:104-117.
Silver et al. (Oct. 31, 1970) "Effects of Polyamines on Membrane Permeability," Annals of the New York Academy of Sciences. 171(1):838-862.
Smith et al. (Jun. 1, 1982) "Optically active amines. 30. Application of the salicylidenimino chirality rule to aliphatic and alicyclic amines," The Journal of Organic Chemistry. 47(13):2525-2531.
Srivastava et al. (Jul. 21, 2016) "A small-molecule inhibitor of SHIP1 reverses age- and diet-associated obesity and metabolic syndrome," J Clinsight. 1(11):e88544.
Suwa et al. (Oct. 19, 2009) "Discovery and Functional Characterization of a Novel Small Molecule Inhibitor of the Intracellular Phosphatase, SHIP2," British Journal of Pharmacology. 158(3):879-887.
Syhora et al. (May 19, 1965) "Olefine-Forming Elimination of the Amide Group," Tetrahedron Letters. 28:2369-2376.
Taichman et al. (1994) "Human osteoblasts support hematopoiesis through the production of granulocyte colony-stimulating factor," J Exp Mecl. 179:1677-1682.
Taichman et al. (1996) "Human osteoblasts support human hematopoietic progenitor cells in vitro bone marrow cultures," Blood. 87:518-524.
Tesio et al. (Oct. 14, 2013) "Pten loss in the bone marrow leads to G-CSF mediated HSC mobilization," J Exp Med. 210:2337-2349.
Toma et al. (2002) "Human mesenchymal stem cells differentiate to a cardiomyocyte phenotype in the adult murine heart," Circulation. 105:93-98.
Tu et al. (2001) "Embryonic and hematopoietic stem cells express a novel SH2-containing inositol 5'-phosphatase isoform that partners with the Grb2 adapter protein," Blood. 98:2028-2038.
Van Cutsem et al. (2009) "Cetuximab and chemotherapy as initial treatment for metastatic colorectal cancer," N Engl J Med. 360(14):1408-1417.
Viernes et al. (Jul. 2014) "Discovery and development of small molecule SHIP phosphatase modulators," Med Res Rev. 34:795-824.
Vill et al. (Jan. 1, 1994) "Liquid crystalline cholestanyl and cholesteryl ether lipids", Molecular Crystals and Liquid Crystals Science and Technology, Molecular Crystals and Liquid Crystals. 250A:73-83.
Wilson et al. (2008) "Hematopoietic stem cells reversibly switch from dormancy to self-renewal during homeostasis and repair," Cell. 135:1118-1129.
Wong et al. (2010) "Targeting the PI3K signaling pathway in cancer," Current Opinion in Genetics and Development. 87-90.
Wu et al. (Feb. 1, 1992) "Triethylamine-Photosensitized Reduction of a Ketone Via a Chemical Sensitization Mechanism," Journal of the American Chemical Society. 114(5):1812-1816.
Yagi et al (Mar. 1, 1967) "Synthesis of C-3 ureido steroids," The Journal of Organic Chemistry. 32(3):713-718.
Yilmaz et al. (2006) "Pten dependence distinguishes haematopoietic stem cells from leukaemia-initiating cells," Nature. 441:475-482.
Zhang et al. (2006) "Pten maintains haematopoietic stem cells and acts in lineage choice and leukaemia prevention," Nature. 441:518-522.
Zhou et al. (Aug. 7, 2014) "Leptin-receptor-expressing mesenchymal stromal cells represent the main source of bone formed by adult bone marrow," Cell Stem Cell. 15:154-168.
U.S. Appl. No. 15/319,326, filed Jun. 17, 2015, Kerr, William G.
U.S. Appl. No. 15/319,321, filed Jun. 17, 2015, Kerr, William G.
U.S. Appl. No. 15/396,272, filed Dec. 30, 2016, Kerr, William G.
Extended European Search Report from EP 15811231.8 dated Dec. 17, 2017, 11 pp.
Extended European Search Report from EP 15810117.0 dated Dec. 19, 2017, 9 pp.
Balch "A Novel therapeutic approach in breast and hematopoietic cancers: inhibition of SH2-Domain containing inositol 5' phosphatase (SHIP)," May 2013, Syracuse University Honors Program Capstone Projects, Paper 56, 41 pp, Available at https://surface.syr.edu/honors_capstone/56/.
M.G. Hunter et al. "Recruitment to the Granulocyte Colony-Stimulating Factor Receptor Contribute to Hyperproliferative Responses in Severe Congenital Neutropenia/Acute Myelogenous Leukemia," The Journal of Immunology, vol. 173, No. 8, Oct. 6, 2004 (Oct. 6, 2004), pp. 5036-5045, XP055432769, Loss of SHIP and CIS 1-15 US ISSN: 0022-1767, DOI :10.4049/jimmunol.173.8.5036 *abstract*.

* cited by examiner

SHIP INHIBITION TO INDUCE ACTIVATION OF NATURAL KILLER CELLS

CROSS-REFERENCE TO RELATED APPLICATIONS

This application claims priority benefit of U.S. Provisional Patent Application Ser. No. 62/013,511, filed Jun. 17, 2014, the disclosure of which is hereby incorporated by reference herein in its entirety.

FIELD OF THE INVENTION

The present invention relates to the use SHIP inhibitors for the purpose of inhibiting SHIP to induce broad activation of natural killer (NK) cells to treat various diseases.

BACKGROUND OF THE INVENTION

Natural Killer Cells (or NK cells) are a type of cytotoxic lymphocyte critical to the innate immune system. The role NK cells play is analogous to that of cytotoxic T cells in the vertebrate adaptive immune response. NK cells provide rapid responses to virally infected cells and respond to tumor formation, acting at around 3 days after injection. Typically immune cells detect MHC (major histocompatibility complex) presented on infected cell surfaces, triggering cytokine release, causing lysis or apoptosis. NK cells are unique, however, as they have the ability to recognize stressed cells in the absence of antibodies and MHC, allowing for a much faster immune reaction. They were named "natural killers" because of the initial notion that they do not require activation in order to kill cells that are missing "self" markers of major histocompatibility complex (MHC) class 1.

NK cells (belonging to the group of innate lymphoid cells) are defined as large granular lymphocytes (LGL) and constitute the third kind of cells differentiated from the common lymphoid progenitor generating B and T lymphocytes. NK cells are known to differentiate and mature in the bone marrow (BM), lymph node, spleen, tonsils and thymus where they then enter into the circulation. NK cells differ from Natural Killer T cells (NKT) phenotypically, by origin and by respective effector functions; often NKT cell activity promotes NK cell activity by secreting IFNγ. In contrast to NKT cells, NK cells do not express T-cell antigen receptors (TCR) or Pan T marker CD3 or surface immunoglobulins (Ig) B cell receptors, but they usually express the surface markers CD16 (FcγRIII) and CD56 in humans, NK1.1 or NK1.2 in C57BL/6 mice. Up to 80% of human NK cells also express CD8.

In addition to the knowledge that natural killer cells are effectors of innate immunity, recent research has uncovered information on both activating and inhibitory NK cell receptors which play important function roles including self tolerance and sustaining NK cell activity. NK cell also play a role in adaptive immune response, numerous experiments have worked to demonstrate their ability to readily adjust to the immediate environment and formulate antigen-specific immunological memory, fundamental for responding to secondary infections with the same antigen. The ability for NK cells to act in both the innate and adaptive immune response is becoming increasingly important in research utilizing NK cell activity and potential cancer therapies.

NK cell receptors can also be differentiated based on function. Natural cytotoxicity receptors directly induce apoptosis after binding to ligands that directly indicate infection of a cell. The MHC dependent receptors (described above) use an alternate pathway to induce apoptosis in infected cells. Natural killer cell activation is determined by the balance of inhibitory and activating receptor stimulation i.e. if the inhibitory receptor signaling is more prominent then NK cell activity will be inhibited, similarly if the activating signal is dominant then NK cell activation will result.

Activating receptors: Ly49 (homodimers)—a relatively ancient, C-type lectin family receptor; are of multigenic presence in mice, while humans have only one pseudogenic Ly49; the receptor for classical (polymorphic) MHC I molecules. NCR (natural cytotoxicity receptors), upon stimulation, mediate NK killing and release of IFNγ. CD94:NKG2 (heterodimers)—a C-type lectin family receptor, conserved in both rodents and primates and identifies non-classical (also non-polymorphic) MHC I molecules like HLA-E. Expression of HLA-E at the cell surface is dependent on the presence of nonamer peptide epitope derived from the signal sequence of classical MHC class 1 molecules, which is generated by the sequential action of signal peptide peptidase and the proteasome. Though indirect, this is a way to survey the levels of classical (polymorphic) HLA molecules. CD16 (FcγIIIA) play a role in antibody-dependent cell-mediated cytotoxicity (ADCC), in particular they bind IgG.

Inhibitors Receptors: KIR (Killer-cell immuoglobulin-like receptors)—belong to a multigene family of more recently-evolved Ig-like extracellular domain receptors; are present in non-human primates; and are the main receptors for both classical MHC 1 (HLA-A, HLA-B, HLA-C) and also non-classical HLA-G in primates. Some KIRs are specific for certain HLA subtypes. Most KIR are inhibitory and dominant. Regular cells express MHC class 1 and therefore are recognized by KIR receptors and NK cell killing is inhibited. ILT or LIR (leukocyte inhibitory receptors)—are recently-discovered members of the Ig receptor family. Ly49 (homodimers)—a C-type lectin family of receptors. Are of multigenic presence in mice, while humans have only one pseudogenic Ly49. Both activating and inhibitory isoforms exist. Highly polymorphic on the population level. Even though they are structurally unrelated to KIR:s, they are the functional homologues of KIR:s in mice, including the expression pattern, Ly49:s are receptor for classical (polymorphic) MHC I molecules.

NK cell function: Cytolytic granule mediated cell apoptosis: NK cells are cytotoxic; small granules in their cytoplasm contain proteins such as perforin and proteases known as granzymes. Upon release in close proximity to a cell slated for killing, perforin forms pores in the cell membrane of the target cell, creating an aqueous channel through which the granzymes and associated molecules can enter, inducing either apoptosis or osmotic cell lysis. The distinction between apoptosis and cell lysis is important in immunology: lysing a virus-infected cell could potentially only release the virions, whereas apoptosis leads to destruction of the virus inside, α-defensins, an antimicrobial is also secreted by NK cells, directly kills bacteria by disrupting their cell walls analogous to neutrophils.

Antibody-dependent cell-mediated cytotoxicity (ADCC): Infected cells are routinely opsonized with antibodies for detection by immune cells. Antibodies that bind to antigens can be recognized by FcγRIII (CD16) receptors expressed on NK cells resulting in NK activation, release of cytolytic granules and consequent cell apoptosis. This is a major mechanism of killing for some monoclonal antibodies like rituximab (Rituxan), ofatumumab (Azzera) and others.

Cytokine-induced NK and CTL activation: Cytokines play a crucial role in NK cell activation. As these are stress molecules released by cells upon viral infection, they serve to signal to the NK cell the presence of viral pathogens. Cytokines involved in NK activation include IL-12, IL-15, IL-18, IL-2, and CCL5. NK cells are activated in response to interferons or macrophage-derived cytokines. They serve to contain viral infections while the adaptive immune response is generating antigen-specific cytotoxic T cells that can clear the infection. NK cells work to control viral infections by secreting IFNγ and TNFα. IFNγ activates macrophages for phagocytosis and lysis, and TNFα acts to promote direct NK tumor cell killing. Patients deficient in NK cells prove to be highly susceptible to early phases of herpes virus infection.

Tumor cell surveillance: Natural killer cells often lack antigen-specific cell surface receptors and therefore are part of innate immunity, i.e. able to react immediately with no prior exposure to the pathogen. In both mice and humans, NKs can be seen to play a role in tumor immuno-surveillance by directly inducing the death of tumor cells (NKs act as cytolytic effector lymphocytes), even with the absence of surface adhesion molecules and antigenic peptides. This role of NK cells is critical for immune success particularly because T cells are unable to recognize pathogens in the absence of surface antigens. Tumor cell detection results in activation of NK cells and consequent cytokine production and release.

If the tumor cells do not cause inflammation, they will also be regarded as self and therefore will not induce a T cell response. A number of cytokines are produced by NKs, including tumor necrosis factor α (TNFα), IFNγ, and interleukin (IL-10). TNFα and IL-10 act as pro-inflammatory and immuno-suppressors, respectively. The activation of NK cells and subsequent production of cytolytic effector cells impacts macrophages, dendritic cells, and neutrophils, which subsequently affects antigen-specific T and B cell responses. Instead of acting via antigen-specific receptors, lysis of tumor cells by NK cells is mediated by alternative receptors, including NKG2D, NKp44, NKp46, NKp30, and DNAM. NKG2D is a disulfide-linked homodimer which recognizes a number of ligands, including ULBP and MICA, which are typically expressed on tumor cells.

NK cells, along wall macrophages and several other cell types, express the Fc receptor (FcR) molecule (FC-gamma-RIII=CD16), an activating biochemical receptor that binds the Fc portion of antibodies. This allows NK cells to target cells against which a humoral response has been mobilized and to lyse cells through antibody-dependent cellular cytotoxicity (ADCC). To determine the ADCC contribution of monoclonal antibodies, NK-92 cells (a "pure" NK cell line) has been transacted with the gene for the high-affinity FcR.

Anti-cancer therapies using expanded NK cells: NK cells are currently being used in multiple clinical trials to treat several different types of cancer. Current protocols include treating cancer patients with ex vivo IL-2 expanded NK cells and treating patients with the monoclonal antiKIR antibody, 1-7F9, designed to block NK cell inhibitory receptors. Because of the limited number of NK cells in blood (only 10% of lymphocytes are NK-cells) their number needs to be expanded in culture. This can take a few weeks and the yield is donor dependent. Treating large numbers of patients with IL-2 expanded NK cells is expensive and may not be feasible to do on a large scale. Treating patients with 1-7F9 mAb, by design, may not necessarily result in sustained NK cell activation.

There is a need to develop new methods of inducing broad activation of NK cells to treat or prevent various diseases or conditions.

The present invention is directed to overcoming these and other deficiencies in the art.

SUMMARY OF THE INVENTION

In one aspect, the present invention relates to a method of activating natural killer (NK) cells in a subject suffering from an illness or condition for which NK cells provide a host defense. In one embodiment, this method involves administering a safe and effective amount of a SHIP1 inhibitor or a pan-SHIP1/2 inhibitor to the subject.

These and other objects, features and advantages of this invention will become apparent from the following detailed description of the various aspects of the invention taken in conjunction with the accompanying drawings.

BRIEF DESCRIPTION OF THE DRAWINGS

For the purpose illustrating aspects of the present invention, there are depicted in the drawings certain embodiments of the invention. However, the invention is not limited to the precise arrangements and instrumentalities of the embodiments depicted in the drawings. Further, as provided, like reference numerals contained in the drawings are meant to identify similar or identical elements.

FIG. 4A; 5×10$^5$ GFP expressing RMA-Rae1 cells were injected into C57BL/6 mice. Mice were treated with either SHIPi or vehicle for two days. Peritoneal lavage was performed on the third day and cells collected by lavage were analyzed by flow cytometry. Flow cytometry plots indicated GFP positive cells after removal of dead cells and non-singlets via electronic gating. FIG. 4B: Graph represents poled data from two independent experiments using at least 4 SHIPi treated mice and 4 vehicle treated mice in each experiment.

FIG. 5A: $5\times10^5$ GFP expressing RMA-Rae1 cells were injected into C57BL/6 once or RAG1$^{-/-}$ mice. Mice were treated with either SHIPi or vehicle for two days. Peritoneal lavage was performed on the third day and cells collected by lavage were analyzed by flow cytometry. Flow cytometry plots indicated GFP positive cells after removal of dead cells and nom-singlets via electronic gating. FIG. 5B: Graph summarizes data from 5 SHIPi treated C57BL/6 mice, 5 SHIPi treated RAG1$^{-/-}$ mice, 5 vehicle treated C57BL/6 mice, and 5 vehicle treated RAG1$^{-/-}$ mice.

FIGS. 6A-D: $5\times10^5$ GFP expressing RMA-Rae1 cells were injected into C57BL/6 mice. Mice were treated for two days with SHIPi or vehicle alone. Peritoneal lavage was performed on the third day. Cells collected by lavage were stained with anti-NK1.1, anti-CD3ε, anti-CD19, anti-CD11b and anti-GR1 antibodies and were analyzed by flow cytometry. All populations were determined after backgating on singlets and viable cells. NK cells are NK1.1$^+$CD3ε$^-$CD19$^-$, T cells are CD3ε$^+$NK1.1$^-$CD19$^-$, B cells are CD19$^+$NK1.1$^-$CD3ε$^-$ and myeloid cells are CD11b$^+$GR1$^+$. FIG. 6B: Graph represents pooled data from two independent experiments using at least 4 SHIPi treated mice and 4 vehicle treated mice in each experiment.

DETAILED DESCRIPTION OF THE INVENTION

Figure 1:
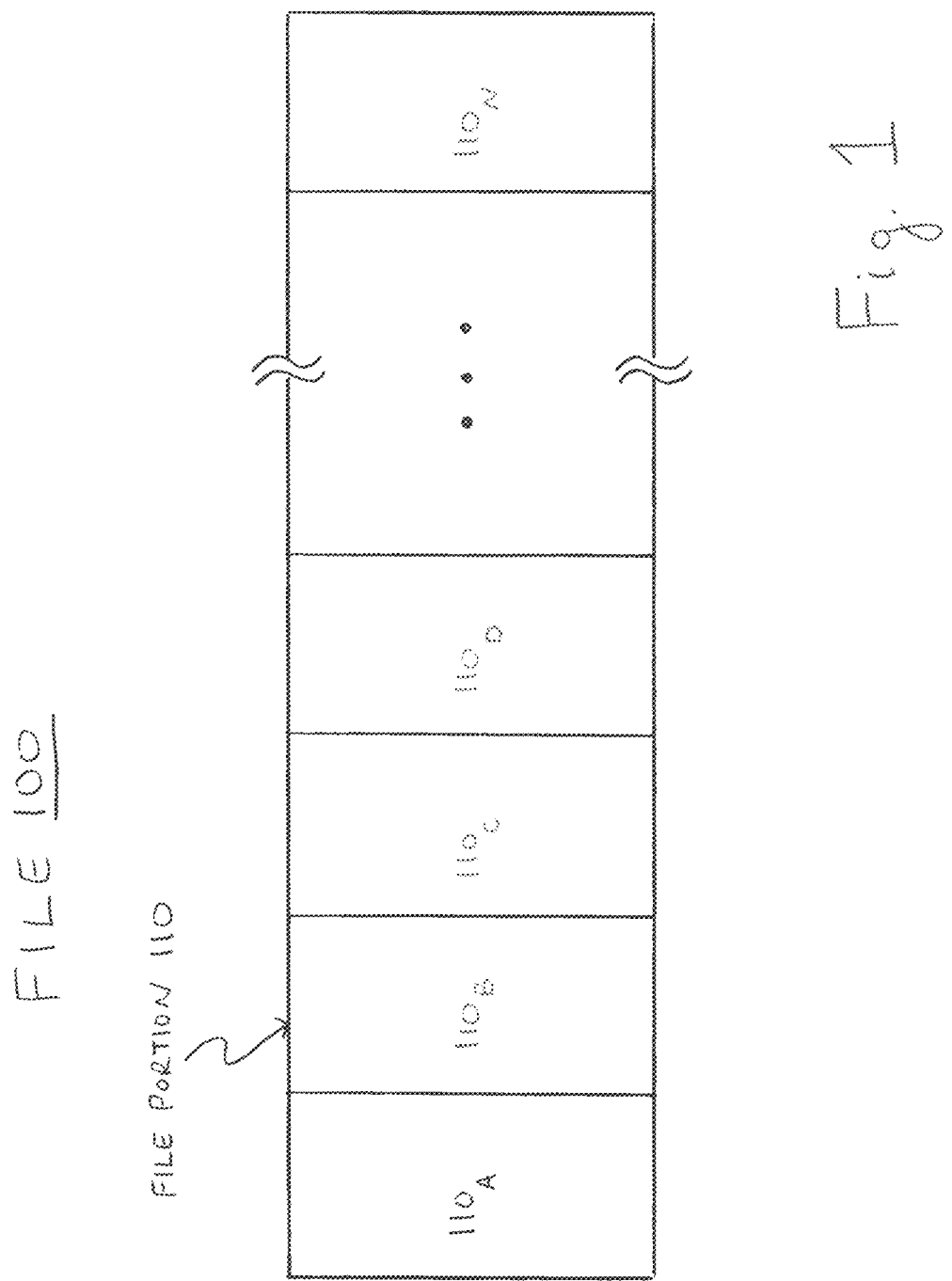
FIG. 1: NK cells harvested from two day SHIPi or vehicle treated mice produced significantly increased IFNγ following stimulation with either anti-NK1.1, anti-NKp46 or anti-NKG2D antibody. Importantly we do not see a significant difference in IFNγ production from NK cells that were unstimulated or from NK cells that were stimulated with PMA and ionomycin, n>=4 mice for each stimulation condition. This graph is representative of at least 3 independent experiments for all stimulation conditions; all of which showed SHIPi treatment significantly increases IFNγ production when cells are stimulated with anti-NK1.1, anti-NKp46 or anti-NKG2D antibody.

The present invention generally relates to new uses of SHIP inhibitors for therapeutic purposes. More particularly, the present invention relates to the use of SHIP inhibitors, including, without limitation, SHIP1 and/or pan-SHIP1/2 inhibitors, for the inhibition of SHIP to induce broad activation of natural killer (NK) cells to treat various diseases.

In one aspect, the present invention relates to a method of using SHIP1 inhibitors and pan-SHIP1/2 inhibitors to induce broad activation of NK cells, thereby treating various diseases (e.g., cancers) as disclosed or contemplated herein. In one embodiment, this method involves administering a SHIP1 inhibitor or a pan-SHIP1/2 inhibitor to a subject to induce broad activation of NK cells in the subject in an amount effective to treat the subject for a disease affected by NK cells (e.g., cancers or other diseases disclosed or contemplated herein).

In one embodiment of this method, the present invention relates to a method of activating NK cells in a subject suffering from an illness or condition for which NK cells provide a host defense. This embodiment of the method involves administering a safe and effective amount of a SHIP1 inhibitor or a pan-SHIP1/2 inhibitor to the subject.

Suitable SHIP inhibitors are described in more detail herein below. Further, suitable SHIP inhibitors and synthetic pathways for various suitable SHIP inhibitors are described in WO 2011/127465 A2 to Kerr et al. and WO 2015/003063 A1 to Kerr et al., the disclosures of which are incorporated by reference herein in their entirety.

According to various embodiments, the substance suitable for the instant invention can be a nucleic acid, such as a genetic construct or other genetic means directing expression of an antagonist of SHIP function. Nucleic acid molecules suitable for the inventive method include anti-sense polynucleotides, other polynucleotides that bind to SHIP mRNA, recombinant retroviral vector, or a combination thereof. A preferred genetic construct of the invention comprises a gene delivery vehicle, a recombinant retroviral vector, or a combination thereof. In a preferred embodiment, the substance that inhibits SHIP function is a nucleic acid that hybridizes to a SHIP mRNA.

In other embodiments, the substances suitable for the instant invention may also include peptidomimetic inhibitors of SHIP function, ribozymes, and an RNA aptamer, or a combination thereof.

Pharmaceutical agents or generic therapies that reduce or eliminate SHIP activity and function encompass, but are not limited to the following: 1) small molecule inhibitors (preferably having a molecular weight of less than 10,000) of SHIP enzymatic activity (i.e. suicide substrates; competitive or non-competitive inhibitors of SHIP activity; RNA aptamers; or PIP 3, 4, or 5 analogs), 2) anti-sense oligonucleotides, 3) peptidomimetics, 4) ribozymes, 5) means for interfering with transcription and/or translation of SHIP RNA, or 6) genetic therapy comprising transfection with a dominant negative SHIP mutant. These agents and/or genetic therapies can exert their effects by preventing the recruitment of SHIP to complexes with other signal transduction components or to the plasma membrane where SHIP can access its inositol phospholipid substrates.

Within the present disclosure, the following terms are to be understood as follows:

An "isolated polypeptide" or "isolated polynucleotide" as used herein refers to a polypeptide or polynucleotide, respectively, produced in vivo or in vitro in an environment manipulated by humans using state of the art techniques of molecular biology, biochemistry and gene therapy. For example, an isolated polypeptide can be produced in a cell free system by automated peptide or polypeptide synthesis, in heterologous host cells transformed with the nucleic acid sequence encoding the polypeptide and regulatory sequences for expression in the host cells, and in an animal into which the coding sequence of the polypeptide has been introduced for expression in the animal. A polypeptide or polynucleotide is "isolated" for purposes herein to the extent that it is not present in its natural state inside a cell as a product of nature. For example, such isolated polypeptides or polynucleotides can be 10% pure, 20% pure, or a higher degree of purity.

The term "inositol polyphosphate 5-phosphatase" as used herein refers to a family of phosphatases each of which removes the 5 phosphate from inositol- and phosphatidylinositol-polyphosphates. The family of proteins is determined by the substrate specificity of these enzymes and by amino acid sequence homology. A description of some of the aspects of the family is provided in Jefferson and Majerus, J Biol Chem 270: 9370-77 (1995). The term "activated T cell" and "activated B cell" refers to T and B cells that nave been stimulated, for example, with cytokines or growth factors, or which have had their antigen receptors cross-linked using antibodies, all of which events stimulate gene expression, cell proliferation, or other responses in T and B cells.

The term "tyrosine phosphorylated" as used herein refers to the addition of a phosphate group at a tyrosine residue. Generally, tyrosine phosphorylation of polypeptides is associated with activation or inactivation of signaling pathways. Tyrosine phosphorylation is also associated with activation or inhibition of signaling molecules. Tyrosine phosphorylation of a polypeptide of the invention can occur in response to, for example, B or T cell activation. In some cases, binding to other polypeptides occurs before, after, or during the tyrosine phosphorylation of a polypeptide.

The term "apparent molecular weight" as used herein refers to the molecular weight of the protein or polypeptide as it migrates on a polyacrylamide gel under reducing or non-reducing conditions. The "apparent" molecular weight may be accounted for by glycosylations or other moieties that alter the molecular weight of the polypeptide alone.

The term "SHIP" as used herein refers to SH2-containing inositol-5-phosphatase. SHIP may have an apparent molecular weight of about 145 kDa and is expressed in at least hemopoietic cells. It contains an amino-terminal src-homology domain (SH2), a central 5'-phophoinositol phosphatase domain, two phosphotyrosine binding consensus sequences, and a proline-rich region at the carboxyl tail.

The term at "means for inhibiting SHIP function" comprises genetic and non-genetic means for inhibiting SHIP function, and includes substances that inhibit SHIP functions.

Among the genetic construct inhibiting SHIP function are various "gene delivery vehicles" known to those of skill in the art, that facilitate delivery to a cell of, for example, a coding sequence for expression of a polypeptide, such as a SHIP inhibitor, an anti-sense oligonucleotide, an RNA aptamer capable of inhibiting SHIP enzymatic activity, an RNA aptamer capable of inhibiting a ribozyme, or another genetic construct of inhibiting SHIP activity known to those of skill in the art.

Among the non-genetic means inhibiting SHIP function are pharmaceutical agent pharmaceutically acceptable safe thereof that are preferably administered in a pharmaceutically acceptable carrier.

According to preferred embodiments, substances suitable for the instant invention can be a nucleic acid, such as a genetic construct or other genetic means directing expression of an antagonist of SHIP function. Nucleic acid molecules suitable for the inventive method include anti-sense polynucleotides, other polynucleotides that bind to SHIP mRNA, recombinant retroviral vector, or a combination thereof. A preferred genetic construct of the invention comprises a gene delivery vehicle, a recombinant retroviral vector, or a combination thereof. In a preferred embodiment, the substance that inhibits SHIP function is a nucleic acid that hybridizes to a SHIP mRNA.

Preferred substances may also include peptidomimetic inhibitors of SHIP function, ribozymes, and an RNA aptamer, or a combination thereof.

Suitable substances for the instant inversion may also be a low molecular weight substance having a molecular weight of less than about 10,000 that inhibits SHIP activity.

The cell to which said component or substance is delivered can be within a mammal, as in in vivo gene therapy or can be removed from a mammal for transfection, or administration of a pharmaceutical agent and can be subsequently returned to the mammal, as, for example, in ex vivo therapy or ex vivo gene therapy. The delivery vehicle can be any component of vehicle capable of accomplishing the delivery of a gene or substance to a cell, for example, a liposome, a particle, naked DNA, or a vector. A gene delivery vehicle is a recombinant vehicle, such as a recombinant viral vector, a nucleic acid vector (such as plasmid), a naked nucleic acid molecule such as a gene, a nucleic acid molecule complexed to a polycationic molecule capable of neutralizing the negative charge on the nucleic acid molecule and condensing the nucleic acid molecule into a compact molecule, a nucleic acid associated with s liposome (Wang, et al., PNAS 84:7851, 1987), and certain eukaryotic cells such as a producer cell, that are capable of delivering a nucleic acid molecule having or more desirable properties to host cells in an organism. The desirable properties include the ability to express a desired substance, such as a protein, enzyme, or antibody, and/or the ability to provide a biological activity, which is where the nucleic acid molecule carried by the gene delivery vehicle is itself the active agent without requiring the expression of a desired substance. One example of such biological activity is gene therapy where the delivered nucleic acid molecule incorporates into a specified gene so as to inactivate the gene and "turn off" the product the gene was making, or to alter the translation or stability of the mRNA of the specified gene product. Gene delivery vehicle refers to an assembly which is capable of directing the expression of the sequence(s) or gene(s) of interest or of turning off the gene of interest. The gene delivery service will generally include promoter elements and may include a signal that directs polyadenylation. In addition, the gene delivery vehicle can include a sequence which is operably linked to the sequence(s) or gene(s) of interest and, when transcribed, acts as a translation imitation sequence. The gene delivery vehicle may also include a selectable marker such as Neo, SV.sup.2 Neo, TK, hygromycin, phleomycin, histidinol, or DHFR, as well as one or more restriction sites and a translation termination sequence. Gene delivery vehicles as used within the present invention refers to recombinant vehicles, such as viral vectors (Jolly, Cancer Gen. Therapy 1:5164, 1994), nucleic acid vectors, naked DNA, oligonucleotides, cosmids, bacteria, and certain eukaryotic cells (including producer cells; see U.S. Ser. No. 08/240,030 and U.S. Ser. No. 07/800,921), that are capable of eliciting an immune response within an animal. Representative examples of such gene delivery vehicles include poliovirus (Evans et al., Nature 339:385-388, 1989; and Sabin, J. Biol. Standardization 1:115-113, 1973); rhinovirus; pox viruses, such as canary pox virus or vaccinia virus (Fisher-Hoch et al., PNAS 86:317-321, 1989; Flexner et al., Ann. N.Y. Acad. Sci. 569:86-103, 1989; Flexner et al., Vaccine 8:17-21, 1990; U.S. Pat. Nos. 4,603,112, 4,179,330, and 5,017,487; WO 89/01973), SV40 (Mulligan et al., Nature 277:108-114, 1979); retrovirus (U.S. Pat. No. 4,777, 127, GB 2,200,651, EP 0,345,242, and WO 91/02805); influenza virus (Luytjes et al., Cell 59:1107-1113, 1989; McMicheal et al., N. Eng. J. Med. 309:13-17, 1983; and Yap et al., Nature 273:238-239, 1973); adenovirus (Berkner, Biotechniques 6:616-627, 1988; Rosenfeld et al., Science 252:431-434, 1991; WO 93/9191; Kolls et al., PNAS 91:215-219, 1994; Kass-Eisler et al., PNAS 96:11498-11502, 1993; Guzman et. al., Circulation 88:2838-2848, 1993; Guzman et al., Cir. Res. 73:1202-1207, 1993; Zabner et al., Cell 75:207-216, 1913; Li et al., Hum. Gene Ther. 4:403-409, 1993; Caillaud et al., Eur. J. Neurosci. 5:287-1291, 1993; Vincent et al., Nat. Genet. 5:130-134, 1993; Jaffe et al., Nat. Genet. 1:372-378, 1992; and Levrero et al., Gene 101:195-202, 1991); parvovirus such as adeno-associated virus (Samulski et al., J. Vir. 63:3822-3828, 1989; Mendelson et al., Virol. 166:151-165, 1988; PA 7/222,684); herpes (Kit Adv. Exp. Med. Biol. 215:219-234, 1989); SV40; HIV (Poznansky, J. Virol. 65:532-536, 1991); measles (EP 0,440,219); astrovirus (Munroe, S, S. et al., J. Vir. 67:3611-3614, 1993); Semlild Forest Virus, and coronavirus, as well as other viral systems (e.g., EP 0,440,219; WO 92/06693; U.S. Pat. No. 5,166,057). In addition, viral carriers may be homologous, non-pathogenic (defective), replication competent viruses (e.g., Overbaugh et al., Science 239:906-910, 1988) that nevertheless induce cellular immune responses, including cytotoxic T-cell lymphocytes (CTL).

The term "ex vivo administration" refers to transfecting or administering a substance to a cell, for example a cell from a population of cells that are exhibiting aberrant SHIP activity, after the cell is removed from the mammal. After transfection or administration of the substance, the cell is then replaced in the mammal. Ex vivo administration can be accomplished by removing cells from a mammal, optionally selecting cells to transform, rendering the selected cells incapable of replication, transforming or treating the selected cells with a polynucleotide or other means for modulating SHIP activity, and placing the transformed or treated cells back into the mammal.

"Administration" or "administering" as used herein refers to the process of delivering to a mammal a therapeutic agent or a combination of therapeutic agents. The process of administration can be varied, depending on the therapeutic agent, or agents, and the desired effect. Administration can be accomplished by any means appropriate for the therapeutic agent, for example, by parenteral, mucosal, pulmonary, topical, catheter-based, or oral means of delivery. Parenteral delivery can include, for example, subcutaneous, intravenous, intramuscular, intra-arterial, and injection into the tissue of an organ. Mucosal delivery can include, for example, intranasal delivery. Pulmonary delivery can include inhalation of the agent. Catheter-based delivery can include delivery by iontophoretic catheter-based delivery. Oral delivery can include delivery of an enteric coated pill, or administration of a liquid by mouth. Administration will generally also include delivery with a pharmaceutically acceptable carrier, such as, for example, a buffer, a polypeptide, a peptide, a polysaccharide conjugate, a liposome and/or a lipid. Gene therapy protocol is considered an administration in which the therapeutic agent is a polynucleotide capable of accomplishing a therapeutic goal when expressed as a transcript or a polypeptide in the mammal.

A "nucleic acid" or a "polynucleotide," as used herein, refers to either RNA or DNA molecule that encodes a specific amino acid sequence or its complementary strand. Nucleic acid molecules may also be non-coding sequences, for example, a ribozyme, an antisense oligonucleotide, or an untranslated portion of a gene. A "coding sequence" as used herein, refers to either RNA or DNA that encodes a specific amino acid sequence, or its complementary strand. A polynucleotide may include, for example, an antisense oligonucleotide, or a ribozyme, and can also include such items as a 3' or 5' untranslated region of a gene, or an intron of a gene, or other region of a gene that does not make up the coding region of the gene. The DNA or RNA may be single stranded or double stranded. Synthetic nucleic acids or synthetic polynucleotides can be chemically synthesized nucleic acid sequences, and can also be modified with chemical moieties to render the molecule resistant to degradation. Synthetic nucleic acids can be ribozymes or antisense molecules, for example. Modifications to synthetic nucleic acid molecules include nucleic acid monomers or derivative or modifications thereof, including chemical moieties, such as, for example, phosphothioate modification. A polynucleotide derivative can include, for example, such polynucleotides as branched DNA (bDNA). A polynucleotide can be a synthetic or recombinant polynucleotide, and can be generated, for example, by polymerase chain reaction (PCR) amplification, or recombinant expression of complementary DNA or RNA, or by chemical synthesis.

The term "an expression control sequence" or a "regulatory sequence" refers to a sequence that is conventionally used to effect expression of a gene that encodes a polypeptide and include one or more components that affect expression, including transcription and translation signals. Such a sequence includes, for example, one or more of the following: a promoter sequence, an enhancer sequence, an upstream activation sequence, a downstream termination sequence, a polyadenylation sequence, an optimal 5' leader sequence to optimize initiation of translation in mammalian cells, a Kozak sequence, which identifies optimal residues around initiator AUG for mammalian cells. The expression control sequence that is appropriate for expression of the present polypeptide differs depending upon the host system in which the polypeptide is to be expressed. For example, in prokaryotes, such a control sequence can include one or more of a promoter sequence, a Shine-Dalgarno sequence, a ribosomal binding site, and a transcription termination sequence. In eukarytes, for example, such a sequence can include a promoter sequence, and a transcription termination sequence. If any necessary component of an expression control sequence is lacking in the nucleic acid molecule of the present invention, such a component can be supplied by the expression vector to effect expression. Expression control sequences suitable for use herein may be derived from a prokaryotic source, a eukaryotic source, a virus or viral vector or from a linear or circular plasmid. Further details regarding expression control sequences are provided below. An example of a regulatory sequence is the human immunodeficiency virus ("HIV-1") promoter that is located in the U3 and R region of the HIV-1 long terminal repeat ("LTR"). Alternatively, the regulatory sequence herein can be a synthetic sequence, for example, one made by combining the UAS of one gene with the remainder at a requisite promoter from another gene, such as the GADP/ASH2 hybrid promoter.

"Hybridization" refers to the association of two nucleic acid sequences to one another by specific hydrogen bonding. Typically, one sequence can be fixed to a solid support and the other is free in solution. The two sequences are placed in contact with one another under conditions that favor hydrogen bonding. Factors that affect this binding bonding include: the type and volume of solvent; reaction temperature; time of hybridization; agitation; agents to block the non-specific attachment of the liquid phase sequence to the solid support (Denhardt's reagent or BLOTTO); concentration of the sequences; use of substances to increase the rate of association of sequences (dextran sulfate or polyethylene glycol); and, the stringency of the washing conditions following hybridization. See Sambrook et al. MOLECULAR CLONING: A LABORATORY MANUAL, SECOND EDITION (1989), Volume 2, chapter 9, pages 9.47 to 9.57. "Stringency" refers to conditions in a hybridization reaction that favor association of very similar sequences over sequences that differ. For example, the combination of temperature and salt concentration should be chosen that is approximately 12° to 20° C. below the calculated Tm of the hybrid under study.

The term "naked DNA" refers to polynucleotide DNA for administration to a mammal for expression in the manual or to inhibit SHIP activity. The polynucleotide can be, for example, a coding sequence, and the polynucleotide DNA can be directly or indirectly connected to an expression control sequence that can facilitate the expression of the coding sequence once the DNA is inside a cell. Alternatively, the DNA can direct production of RNA or a polypeptide that inhibits SHIP activity.

"Recombinant retroviral vector" refers to an assembly which is capable of directing the expression of a sequence(s) or gene(s) of interest. Preferably, the retroviral vector construct should include a 5' LTR, a tRNA binding site, a packaging signal, one or more heterologous sequences, an origin of second strand DNA synthesis and a 3' LTR. A wide variety of heterologous sequences may be included within the vector construct including for example, sequences which encode a protein (e.g., cytotoxic protein, disease-associated antigen, immune accessory molecule, or replacement protein), or which are useful in and of themselves (e.g., as ribozymes or antisense sequences). Alternatively, the heterologous sequence may merely be a "stuffer" or "filler" sequence of a size sufficient to allow production of retroviral particles containing the RNA genome. Preferably the heterologous sequence is at least 1, 2, 3, 4, 5, 6, 7 or 8 Kb in length. The retroviral vector construct may also include transcriptional promoter/enhancer or locus defining element(s), or other elements which control gene expression by means such as alternate splicing, nuclear RNA export, post-translational modification of messenger, or post-transcriptional modification of protein. Optionally, the retroviral vector construct may also include selectable markers that confer resistance of recombinant retroviral vector, transduced or transfected, cells to TK, hygromycin, phleomycin, histidinol, or DHFR, as well as one or more specific restriction sites and a translation termination sequence.

A "therapeutically effective amount" is that amount that will generate the desired therapeutic outcome. For example, if the therapeutic effect desired is reduction or suppression of rejection of a transplant, the therapeutically effective amount is that amount that facilitates reduction or suppression of rejection of a transplant. A therapeutically effective amount can be an amount administered in a dosage protocol that includes days or weeks of administration.

The term "pharmaceutically acceptable carrier" refers to a carrier for administration of a therapeutic agent, such as, for example, a polypeptide, polynucleotide, small molecule (preferably a molecule having a molecular weight of less than about 10,000), peptoid, or peptide, refers to any pharmaceutically acceptable carrier that does not itself induce the production of antibodies harmful to the individual receiving the composition, and which may be administered without undue toxicity.

"Vector construct" refers to an assembly which is capable of directing the expression of the sequence(s) or gene(s) of interest. The rector construct can include transcriptional promoter/enhancer or locus defining element(s), or other elements which control gene expression by other means such as alternate splicing, nuclear RNA export, post-translational modification of messenger, or post-transcriptional modification of protein. In addition, the vector construct must include a sequence, which, when transcribed, is operably linked to the sequence(s) or gene(s) of interest and acts as a translation initiation sequence. Optionally, the vector construct may also include a signal which directs polyadenylation, a selectable marker such as Neo, TK, hygromycin, phleomycin, histidinol, or DHFR, as well as one or more restriction sites and a translation termination sequence. In addition, if the vector construct is placed into a retrovirus, the vector construct must include a packaging signal, long terminal repeats (LTRs), and positive and negative strand primer binding sites appropriate to the retrovirus used (if these are not already present).

"Tissue-specific promoter" refers to transcriptional promoter/enhancer or locus defining elements, or other elements which control gene expression as discussed above, which are preferentially active in a limited number of tissue types. Representative examples of such tissue-specific promoters include the PEP-CK promoter, HER2/neu promoter, casein promoter, IgG promoter, Chorionic Embryonic Antigen promoter, elastase promoter, porphobilinogen deaminase promoter, insulin promoter, growth hormone factor promoter, tyrosine hydroxylase promoter, albumin promoter, alphafetoprotein promoter, acetyl-choline receptor promoter, alcohol dehydrogenase promoter, a or β globin promoters, T-cell receptor promoter, or the osteocalcin promoter.

"Mammalian cell" as used herein refers to a subset of eukaryotic cells useful in the invention as host cells, includes human cells, and animal cells such as those from dogs, cats, cattle, horses, rabbits, mice, goats, pigs, etc. The cells used can be genetically unaltered or can be genetically altered, for example, by transformation with appropriate expression vectors, marker genes, and the like. Mammalian cells suitable for the method of the invention are any mammalian cell capable of expressing the genes of interest, or any mammalian cells that can express a cDNA library, cRNA library, genomic DNA library or any protein or polypeptide useful in the method of the invention. Mammalian cells also include cells from cell lines such as those immortalized cell lines available from the American Type Culture Collection (ATCC). Such cell lines include, for example, rat pheochromocytoma cells (PC12 cells), embryonal carcinoma cells (P19 cells), Chinese hamster ovary (CHO) cells, HeLa cells, baby hamster kidney (BHK) cells, monkey kidney cells (COS), human hepatocellular carcinoma cells (e.g., Hep G2), human embryonic kidney cells, mouse sertoli cells, canine kidney cells, buffalo rat liver cells, human lung cells, human liver cells, mouse mammary tumor cells, as well as others. Also included are hematopoetic stem cells, neuronal stem cells such as neuronal sphere cells, and pluripotent or embryonic stem cells (ES cells).

The term "antagonist" as used herein refers to a molecule that blocks signaling, such as for example a molecule that can bind a receptor, but which does not cause a signal to be transduced by the receptor to the cell. In the case of inositol polyphosphatase 5'-phosphatases an antagonist might block signaling by binding, for example, at an SH2 domain on the molecule, or by binding, for example, so as to inhibit its phosphatase activity, in general, an antagonist of a polypeptide is an inhibitor of any biological activity of the polypeptide. A given inhibitor or agonist may target and inhibit one biological activity, while not affecting another non-target activity of the molecule.

As used herein, in one embodiment, a suitable SHIP1 inhibitor for use in the methods of the present invention can include, without limitation, the following SHIP inhibitor compound:

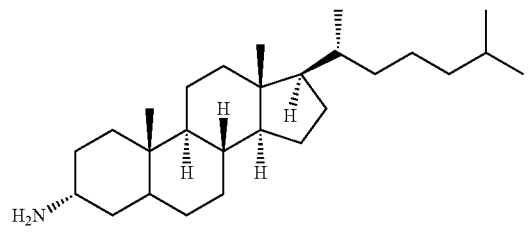

3-α-Aminocholestane (3AC)

As used herein, in other embodiments, suitable SHIP1 inhibitors for use in the methods of the present invention can include, without limitation, the SHIP inhibitor compounds of the formula (I), and pharmaceutical acceptable salts thereof, where formula (I) is its follows;

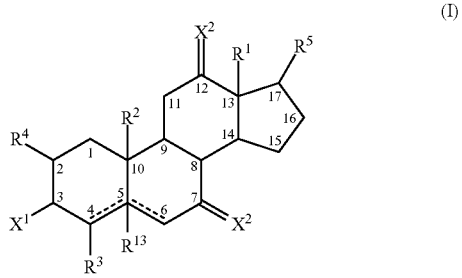

wherein:

----- at the 4,5 and 5,6 positions represents a single or double bond, with the proviso that the sum of double bonds present at the 4,5 and 5,6 positions is 0 or 1.

$R^1$ is a straight chain $C_1$-$C_4$ alkyl or $C_1$-$C_4$ haloalkyl. In one embodiment, $R^1$ is methyl.

$R^2$ s hydrogen, methyl, or halomethyl. In one embodiment, $R^2$ is methyl.

$R^3$ and $R^{13}$ (when present), are individually selected from hydrogen, substituted or unsubstituted amino, $C_1$-$C_4$ alkyl, $C_1$-$C_4$ haloalkyl, and $C_1$-$C_4$ alkenyl. In one embodiment, both $R^3$ and $R^{13}$ are hydrogen.

$R^4$ is hydrogen, hydroxy, substituted or unsubstituted amino, alkyl, or benzyl. In one embodiment, $R^4$ is hydrogen.

$R^5$ represents hydrogen or an alkyl group. In one embodiment, $R^5$ represents an alkyl group. In one embodiment, the alkyl group is 1, 5-dimethylhexyl. In one embodiment, $R^5$ represents two hydrogen atoms or one hydrogen atom together with an alkyl group.

$X^1$ may be selected from the group consisting of hydrogen, hydroxy, mercapto, alkoxy, aryloxy, alkylthio, and arylthio. The alkoxy, aryloxy, alkylthio, and arylthio moieties may be further substituted.

$X^1$ may also be selected from the group consisting of alkylcarbonamido, arylcarbonamido, aminocarbonamido, hydrazinocarbonamido, alkylsulfonamido, arylsulfonamido, aminosulfonamido, and hydrazinosulfonamido, all of which may be further substituted.

$X^1$ may also be selected from the group consisting of ($C_1$-$C_4$ alkyl) carbonyloxy, ($C_1$-$C_4$ alkoxy)carbonyloxy, arylcarbonyloxy, aryloxycarbonyloxy, and aminocarbonyloxy, all of which may be further substituted.

$X^1$ may further be selected from the group consisting of a substituted or unsubstituted amino and secondary and tertiary amino groups that include, at least one $C_1$-$C_4$ alkyl, $C_5$-$C_6$ cycloalkyl, aryl, or heterocyclic substituent, or combinations thereof. In one embodiment, the secondary or tertiary amino group contains at least one $C_1$-$C_4$ alkyl moiety, which may be further substituted.

$X^1$ may further be an aminoalkyl group amino$(CH_2)_n$, where "amino" is an unsubstituted or a substituted secondary or tertiary amino as defined above, and n is an integer from 1 to 4.

$X^1$ may further represent a divalent oxygen moiety, =O, or a divalent N-hydroxyamino moiety, =NOH.

$X^1$ may further be an amino group, except when: $R^1$ and $R^2$ are each methyl; $X^2$, $R^3$, $R^4$, and $R^{13}$ are each hydrogen; and $R^5$ represents one hydrogen atom together with an alkyl group, where the alkyl group is 1, 5-dimethylhexyl alkyl group.

In one embodiment, $X^1$ cannot be hydroxy when: $R^3$ is hydrogen, $R^4$ is hydrogen, and $R^5$ is one hydrogen atom together with an alkyl group.

Each $X^2$ is independently defined to represent a divalent oxo or two hydrogen atoms. In one embodiment, each $X^2$ represents two hydrogen atoms.

The compounds of the present invention, as will be appreciated by one skilled in the art, possess several potential chiral carbon atoms. As a consequence of these chiral centers, the compounds of the present invention may occur as racemates, racemic mixtures, individual diastereomers and substantially pure isomers. All asymmetric forms, individual isomers, and combinations thereof, are within the scope of the present invention.

Throughout this specification, the terms and substituents retain their definitions. Below are particular definitions of terms used herein.

The term "alkyl" by itself or as part of another substituent means, unless otherwise stated, a straight or branched chain hydrocarbon radical and includes straight or branch chain groups such as methyl, ethyl, n-propyl, isopropyl, n-butyl, t-butyl, isobutyl, sec-butyl, and higher homologs and isomers such as n-pentyl, n-hexyl, 2-methylpentyl, 1,5-dimethylhexyl, 1-methyl-4-isopropyl, hexyl and the like. Preferred alkyl groups are those of $C_{20}$ or below (i.e., $C_{1-20}$). A divalent radical derived from an alkane is exemplified by —$CH_2CH_2CH_2CH_2$—. A divalent radical derived from an alkene is exemplified by —CH=CH—$CH_2$—. An example of a non-limiting subset of alkyl is alkyl groups of from 1 to 10 carbon atoms ($C_{1-10}$ alkyl) (e.g., 1, 2, 3, 4, 5, 6, 7, 8, 9, or 10 carbon atoms).

The term "alkenyl" employed alone or in combination with other terms, means a straight chain or branched monounsaturated hydrocarbon group having the stated number of carbon atoms, such as, for example, vinyl, propenyl (allyl), crotyl, isopentenyl, and the various butenyl isomers.

Alkyl and alkenyl groups may include substitutents selected from the group consisting of halo, hydroxy, cyano, mercapto, —S($C_1$-$C_4$ alkyl), amino, substituted amino, acetamido, carboxy, trifluoromethyl, $C_1$-$C_4$ alkoxy, ($C_1$-$C_4$ alkoxy)carbonyl and aminocarbonyl.

The term "cycloalkyl" means an unsubstituted or substituted monovalent saturated cyclic hydrocarbon radical having the stated number of carbon atoms, including, various isomers of cyclopentyl and cyclohexyl. The term "cycloalkenyl" means an unsubstituted or substituted monovalent monounsaturated cyclic hydrocarbon radical having the stated number of carbon atoms, including, various isomers of cyclopentenyl and cyclohexenyl. The term "cycloalkadienyl" means a monovalent diunsatarated cyclic radical having the stated number of carbon atoms, including, the various isomers of cyclopentadienyl and cyclohexadienyl. The substituents can be one or two of the same or different substituents selected from halo, hydroxy, cyano, mercapto, —S($C_1$-$C_4$ alkyl), amino, substituted amino, acetamido, carboxy, trifluoromethyl, $C_1$-$C_4$ alkoxy, ($C_1$-$C_4$ alkoxy)carbonyl and aminocarbonyl.

The dotted lines between the 4,5 and 5,6 positions represent the presence or absence of an additional bond; that is, an unsaturation. Only one unsaturation can be present at any one time. The $R^{13}$ shown in Formula (I) will, of course, be absent when an unsaturation is present.

The term "aryl" means an unsubstituted or substituted monovalent phenyl group. The substituents may be independently selected from halo, —OH, —SH, —S($C_1$-$C_4$) alkyl), $C_1$-$C_5$ alkyl, $C_1$-$C_5$ alkoxy, carboxy, ($C_1$-$C_4$ alkoxy) carbonyl, aminocarbonyl, $C_1$-$C_4$ alkylaminocarbonyl, amino, acetamido, $C_1$-$C_4$ alkylamino, di($C_1$-$C_4$ alkyl)amino or a group —$(CH_2)_q$—R where q is 1, 2, 3, or 4 and R is hydroxy, $C_1$-$C_4$ alkoxy, carboxy, $C_1$-$C_4$ alkoxycarbonyl, amino, aminocarbonyl, $C_1$-$C_4$ alkylamino or di($C_1$-$C_4$ alkyl) amino.

The term "benzyl" means a monovalent group in which a phenyl moiety is substituted by a methylene group. The benzyl group may include further substituents on the phenyl moiety.

The term "amino" means a group —$NH_2$. The term, "substituted amino" means an amino group where one or both amino hydrogens are independently replaced by $C_1$-$C_4$ alkyl, $C_2$-$C_4$ alkenyl, $C_5$-$C_6$ cycloalkyl, $C_5$-$C_6$ cycloalkenyl, aryl, benzyl, or a group —$(CH_2)_q$—R where q is 1, 2, 3, or 4 and R is hydroxy, $C_1$-$C_4$ alkoxy, carboxy, $C_1$-$C_4$ alkoxycarbonyl, amino, aminocarbonyl, $C_1$-$C_4$ alkylamino or di($C_1$-$C_4$ alkyl)amino.

The term "alkylcarbonamido" means a group ($C_1$-$C_4$ alkyl)C(O)N(R)—, where R represents H or $C_1$-$C_4$ alkyl. More specifically, the term "acetamido" means a group $CH_3$C(O)NH—. The term "arylcarbonamido" means a group (aryl)C(O)N(R)—, where R represents H or $C_1$-$C_4$ alkyl. The term "aminocarbonamido" means a group R'R"NC(O)N(R)—, where R represents H or $C_1$-$C_4$ alkyl, and R' and R" independently represent H, $C_1$-$C_4$ alkyl, $C_5$-$C_6$ cycloalkyl, aryl, or heterocyclic.

The term "alkylsulfonamido" means a group ($C_1$-$C_4$ alkyl ($SO_2$N(R)—, where R represents H or $C_1$-$C_4$ alkyl. The term "arylsulfonamido" means a group (aryl)$SO_2$N(R)—, where R represents H or $C_1$-$C_4$ alkyl. The term "aminosulfonamido" means a group R'R"NHSO$_2$N(R)—, where R represents H or $C_1$-$C_4$ alkyl, and R' and R" independently represent H, $C_1$-$C_4$ alkyl, $C_5$-$C_6$ cycloalkyl, aryl, or heterocyclic.

The term "alkylcarbonyloxy" means a group ($C_1$-$C_4$ alkyl)C(O)O—. The term "alkoxycarbonyloxy" means a group ($C_1$-$C_4$ alkyl)OC(O)O—. The term "arylcarbonyloxy" means a group (aryl)C(O)O—. The term "aryloxycarbonyloxy" means a group (aryl)OC(O)O—. The term "aminocarbonyloxy" means a group R'R"NC(O)O—, where R' and R" independently represent H, $C_1$-$C_4$ alkyl, $C_5$-$C_6$ cycloalkyl, aryl, or heterocyclic.

The term "halo" means chloro, bromo, fluoro or iodo. The term "mercapto" means a group —SH.

The term "heterocycle" means an unsubstituted or substituted stable 5- or 6-membered monocyclic heterocyclic ring that consists of carbon atoms and from one to three heteroatoms selected from the group consisting of N, O and S, and wherein the nitrogen, and sulfur heteroatoms may optionally be oxidized, and the nitrogen heteroatom may optionally be quaternized. The heterocyclic ring may be attached, unless otherwise stated, at any heteroatom or carbon atom that affords a stable structure. The heterocycle may be unsubstituted or substituted with one or two substitutes.

In one embodiment of the present invention, the compound of formula (I) is a compound of a formula as set forth below:

Formula 10

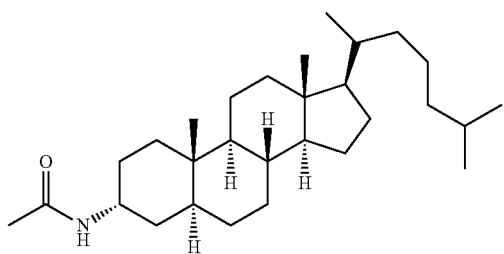

Formula 11

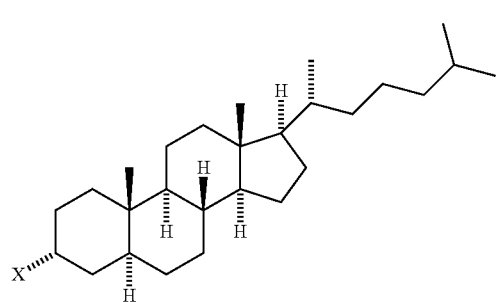

Formula 12

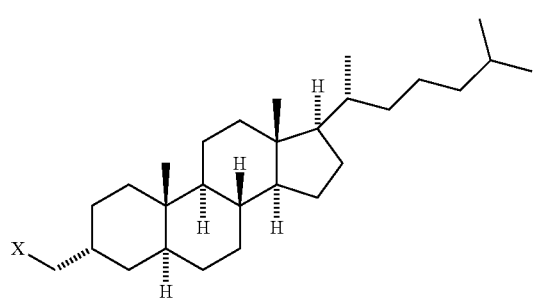

Formula 13

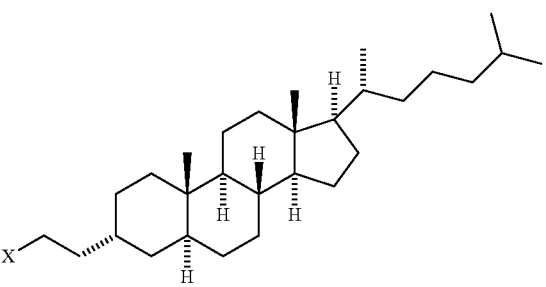

Formula 14

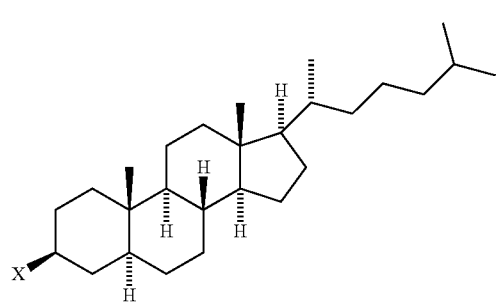

Formula 15
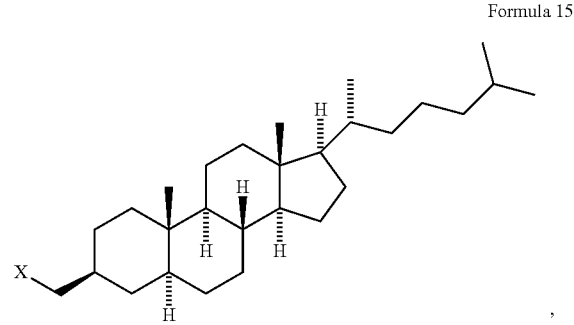
,
Formula 16
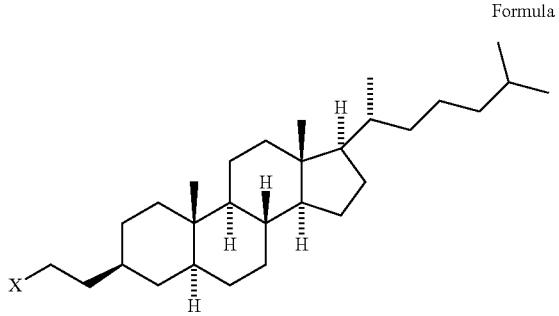
,
Formula 17
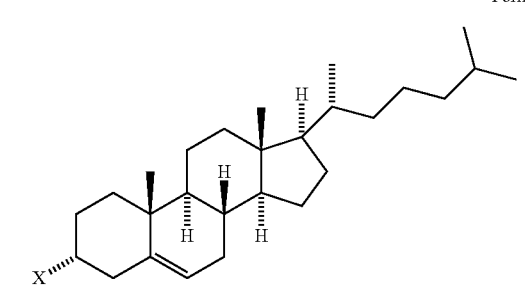
,
Formula 18
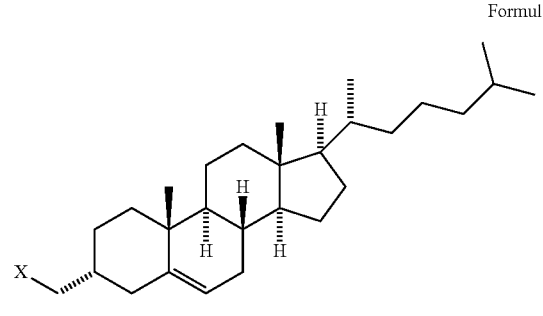
,
Formula 19
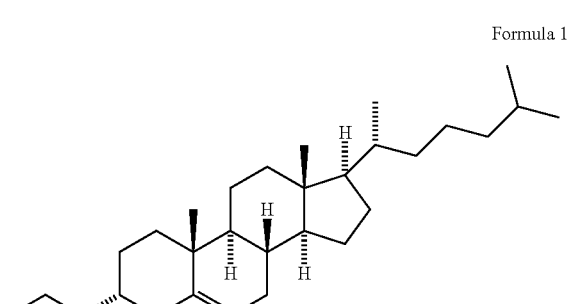
,
Formula 20
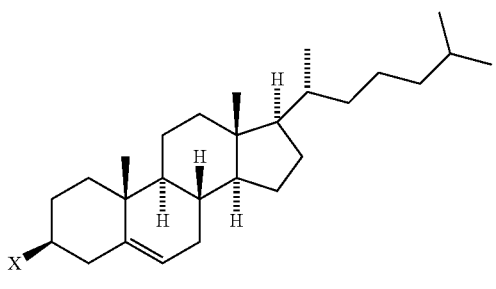
,
Formula 21
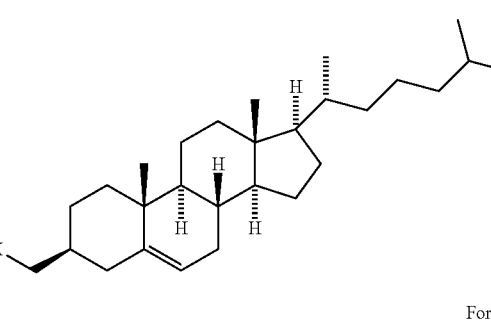
,
Formula 22
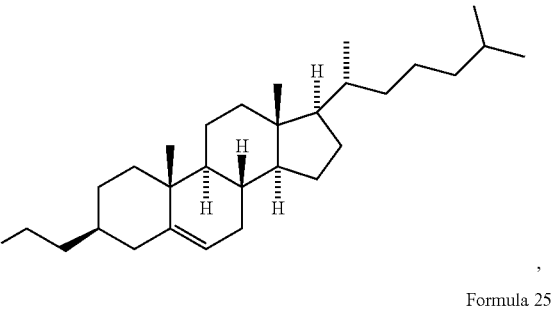
,
Formula 25
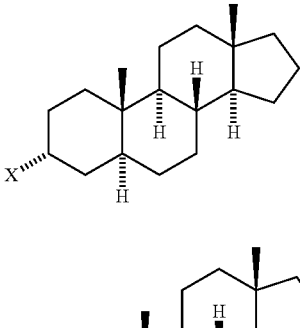
,
Formula 26
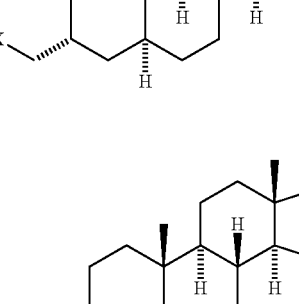
,
Formula 27

-continued

Formula 28

Formula 29

Formula 30

Formula 31

Formula 32

Formula 33

Formula 34

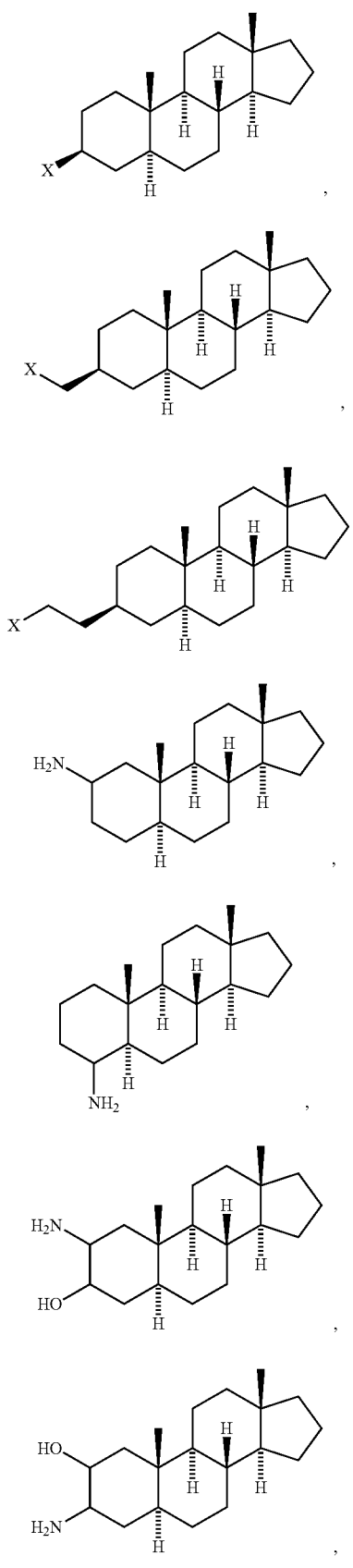

-continued

Formula 35

Formula 36

Formula 37

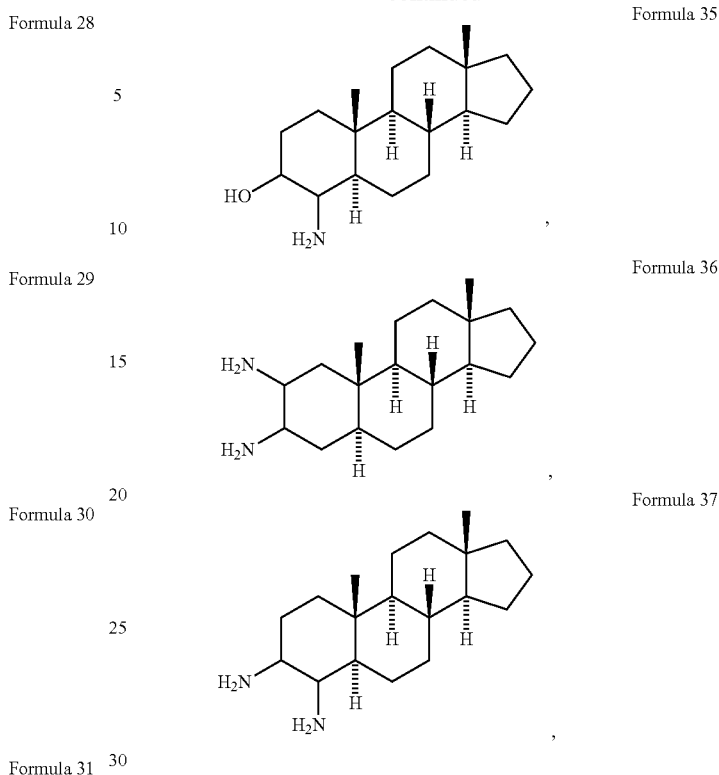

and pharmaceutically acceptable suits thereof, wherein X=NR$_2$, NRCOR, NHCONR$_2$, OR, SR, OCOR, OCONR$_2$, or NHCNHNH$_2$, and wherein R=H, alkyl, cycloalkyl, aryl, or benzyl. In one embodiment, X cannot be NH$_2$ n the compound of Formula 11. In another embodiment, X cannot be hydroxyl in the compound of Formula 20.

In some embodiments, of the invention, the compound of Formula (I) or pharmaceutically acceptable salt thereof is a compound of Formula (IA) or a pharmaceutically acceptable salt thereof:

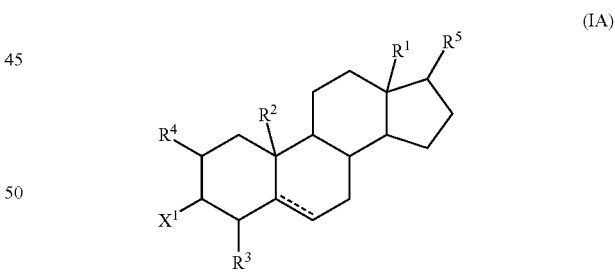

(IA)

wherein

----- represents a single bond double bond (in particular embodiments, ----- represents a single bond);

$R^1$ and $R^2$ are individually selected from hydrogen and $C_{1-3}$ alkyl, (e.g., methyl);

$R^3$ is selected from hydrogen and amino;

$R^4$ is selected from hydrogen, amino, and hydroxy;

$R^5$ is selected from hydrogen, a divalent oxo atom, and $C_{1-10}$ alkyl (e.g., $C_1$-$C_8$ alkyl, such as, for example, $C_8$ alkyl, e.g., 5-dimethylhexyl); and $X^1$ is selected from hydrogen, amino, and hydroxy. In some embodiments, $X^1$ is selected from hydrogen and amino. In a particular embodiment, $X^1$ is amino.

In some embodiments, the compound of Formula (IA) or salt thereof is selected from a compound of Formula (IB) or (IC) below, or a pharmaceutically acceptable salt thereof:
(IB)
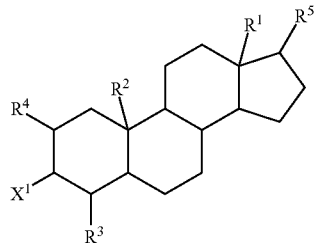
(IC)
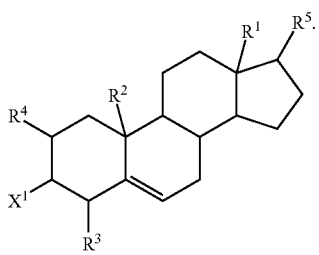
In some embodiments, the compound of Formula (IA) or salt thereof is selected from a compound of Formula (ID)-(IO) below, or a pharmaceutically acceptable salt thereof:
(ID)
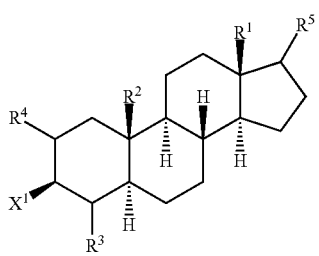
(IE)
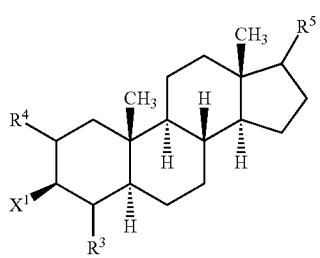
(IF)
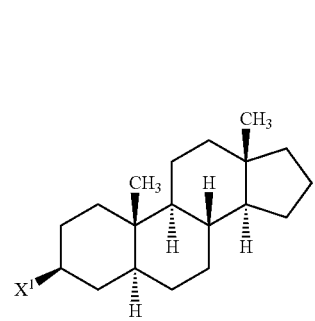
(IG)
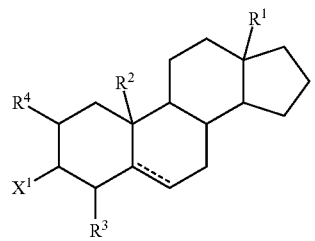
(IH)
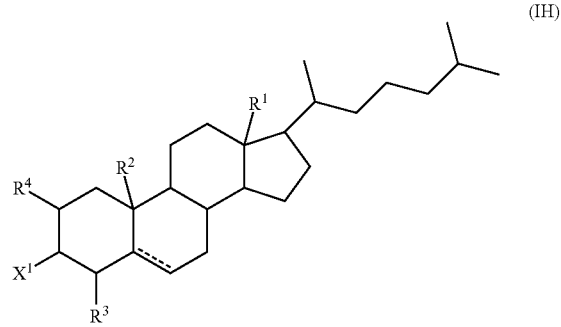
(II)
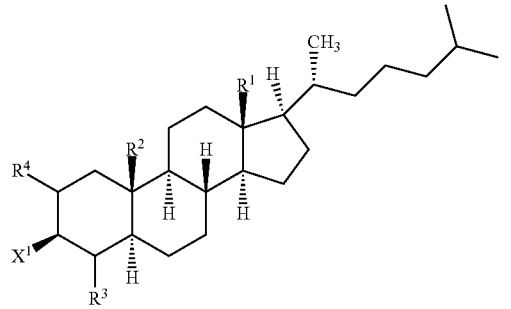
(IJ)
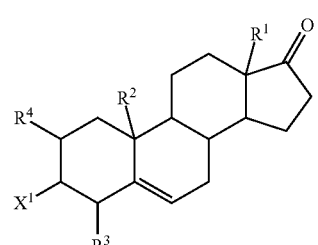
(IK)
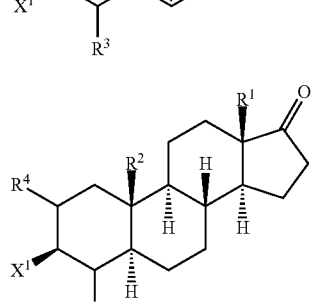
(IL)
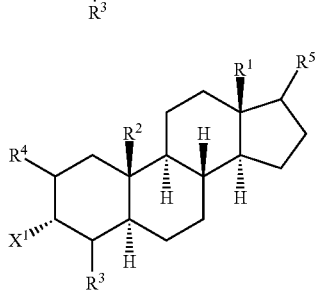

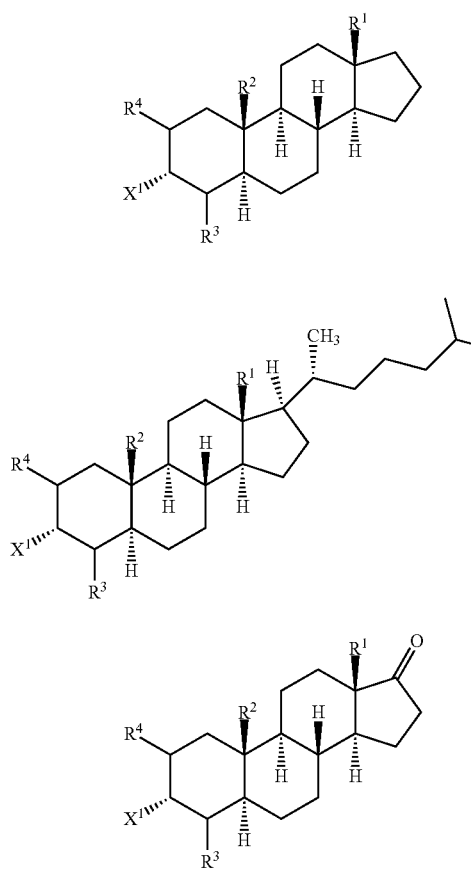

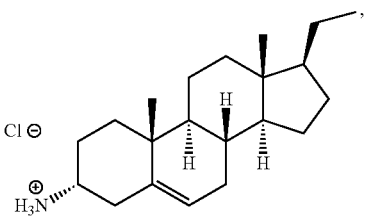

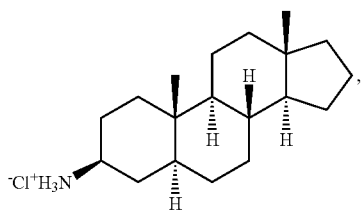

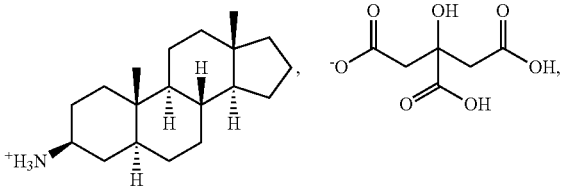

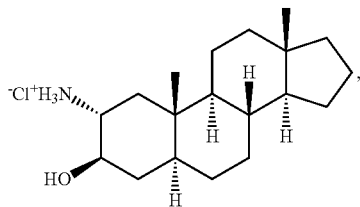

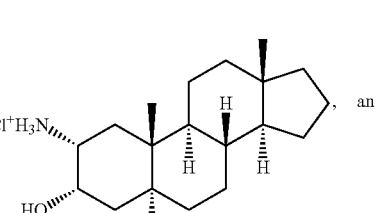

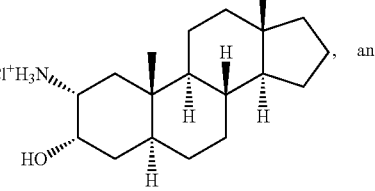

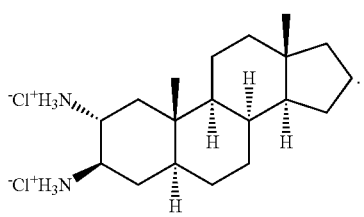

In some embodiments, the inventive method comprises administering a pharmaceutically acceptable salt of a compound according to any one of Formulas (I) or (IA-IO). In some embodiments, the pharmaceutically acceptable salt is a hydrochloride salt. In some embodiments, the pharmaceutically acceptable salt is a salt of a compound wherein $X^1$ is amino (for example, a hydrochloride salt of such a compound, e.g., the pharmaceutically acceptable salt may be a compound having $NH_3Cl$ at the $X^1$ position).

In some non-limiting embodiments, the inventive method comprises administering a compound of Formula (I) (or any sub-genus thereof) as described herein, or a pharmaceutically acceptable salt thereof, with the proviso that if $X^1$ is hydroxy, then $R^4$ is a hydrogen, substituted or unsubstituted amino, $C_1$-C4 alkyl or benzyl.

In some non-limiting embodiments, the inventive method comprises administering a compound of Formula (I) (or any sub-genus thereof) as described herein, or a pharmaceutically acceptable salt thereof, with the proviso that if $X^1$ is hydroxy, at least one of $R^3$ and $R^4$ is other than hydrogen.

In some non-limiting embodiments, the inventive method comprises administering a compound of Formula (I) (or any sub-genus thereof) as described herein, or a pharmaceutically acceptable salt thereof, with the proviso that if $X^1$ is hydroxy, $R^5$ is not an alkyl group.

In some embodiments, the inventive method comprises administering a compound selected from one of the following:

The "SHIP inhibitor compounds" of the present invention are also referred to herein as "SHIP inhibitors," "SHIP1 inhibitors," "SHIP1 inhibitor compounds," "pan-SHIP1/2 inhibitors," and the like. In one embodiment, the SHIP inhibitor compounds of the present invention are selective inhibitors of SHIP1.

As used herein, suitable pan-SHIP1/2 inhibitors for use in the methods of the present invention can include, without limitation, the pan-SHIP1/2 inhibitor compounds as follows:

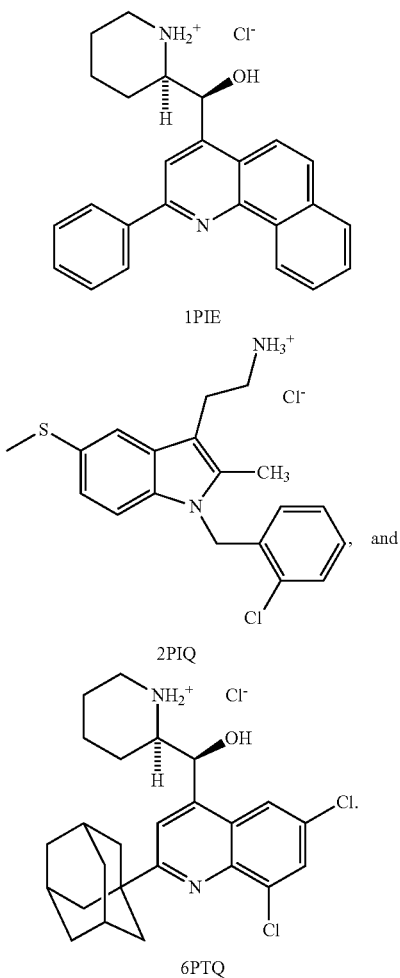

1PIE

2PIQ

6PTQ

Various aspects and embodiments of the present invention as they relate to the SHIP1 and pan-SHIP1/2 inhibitors are further described in the Examples and the associated figures and tables provided herewith in connection with the Examples.

As used herein, in other embodiments, suitable SHIP1 inhibitors for use in the methods of the present invention can include, without limitation, small interfering RNAs (siRNAs) or microRNAs (miRNAs) that are effective to inhibit SHIP1 via RNA interference (RNAi) (post transcriptional gene silencing).

RNAi technology provides an efficient means for blocking expression of a specific gene. RNAi technology takes advantage of the cell's natural machinery, facilitated by short interfering RNA molecules, to effectively knock down expression of a gene of interest. There are several ways to induce RNAi, synthetic molecules, siRNA, miRNA, RNAi vectors, and in vitro dicing.

RNAi can be used to inhibit the SHIP1 genes, such as by creating siRNAs or miRNAs having the appropriate sequence and delivering them to the cells in which inhibition of the SHIP1 gene is desired. A key area of research in the use of RNAi for clinical applications is the development of a safe delivery method, which to date has involved mainly viral vector systems similar to those suggested for gene therapy. Once developed, these delivery methods can be used for the purposes of the present invention. RNAi inducing agents can also be delivered using bacteria, retroviruses, DNA viruses, lipidoids and amphoteric liposomes.

General rules for selecting siRNA targets on mRNA sequences include, for example, the following (www.rnai-web.com/RNAi/siRNA_Design/): (i) Targets should be located 50-100 nt downstream of the start codon (ATG); (ii) Search for sequence motif $AA(N_{19})TT$ or $NA(N_{21})$, or $NAR(N_{17})YNN$, where N is any nucleotide, R is purine (A, G) and Y is pyrimidine (C, U); (iii) Target sequences should have a G+C content between 35-60%; (iv) Avoid stretches of 4 or more nucleotide repeats; (v) Avoid 5'UTR and 3'UTR, although siRNAs targeting UTRs have been shown to successfully induce gene silencing; and (vi) Avoid sequences that share a certain degree of homology with other related or unrelated genes.

Selecting targets for miRNA: In animals, the tendency of miRNAs to bind their mRNA targets with imperfect sequence homology poses considerable challenges with target prediction. In animals, target sites are often only partially complementary to their miRNAs and are mostly located in the 3'UTR of target genes. Several computational approaches have been developed to facilitate experimental design and predicting miRNA targets. In general, computational target prediction identifies potential binding sites according to base-paring rules and cross species conservation conditions.

The dosage form of the SHIP inhibitor of the present invention may be a liquid solution ready for use or intended for dilution with a preservation solution. Alternatively, the dosage form may be lyophilized or power filled prior to reconstitution with a preservation solution. The lyophilized substance may contain, if suitable, conventional excipients.

Other than in the operating examples, or unless otherwise expressly specified, all of the numerical, ranges, amounts, values and percentages such as those for amounts of materials, times and temperatures of reaction, ratios of amounts, values for molecular weight (whether number average molecular weight ("$M_n$") or weight average molecular weight ("$M_w$"), and others in the following portion of the specification may be read as if prefaced by the word "about" even though the term "about" may not expressly appear with the value amount or range. Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that an combination of these values inclusive of the recited values may be used.

As used herein, the term "pretreating" (or "pretreatment") is intended to mean that a first treatment is administered prior to, or in conjunction with, a second treatment. In other words, the pretreatment may be performed before another, later treatment, thus allowing the pretreatment time to take effect. Alternatively, the pretreatment may be performed or administered simultaneously with a second treatment without a temporal delay. Advantageously, a pretreatment is administered prior to a second treatment.

The term "administration" and variants thereof (e.g., "administering" a compound) in reference to a compound of the invention can also mean introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein can also means that amount of active compound or pharmaceutical agent that elicits the biological or medicinal response in a tissue, system, animal or human that is being sought by a researcher, veterinarian, medical doctor or other clinician.

A "subject in need of treatment" is a mammal with a bone-loss condition.

A "pharmaceutically acceptable" component is one that is suitable for use with humans and/or animals without undue adverse side effects (such as toxicity, irritation, and allergic response) commensurate wall a reasonable benefit/risk ratio.

A "safe and effective amount" refers to the quantity of a component that is sufficient to yield a desired therapeutic response without undue adverse side effects (such as toxicity, irritation, or allergic response) commensurate with a reasonable benefit/risk ratio when used in the manner of this invention.

A "pharmaceutically acceptable carrier" can also refer to a carrier, such as a solvent, suspending agent or vehicle, for delivering the compound or compounds in question to the animal or human. The carrier may be liquid or solid and is selected with the planned manner of administration in mind. Liposomes are also a pharmaceutical carrier. As used hereby "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated.

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

Unless defined otherwise, all technical and scientific terms used herein have the same meaning as commonly understood by one of ordinary skill in the art (e.g., in cell culture, molecular genetics, nucleic acid chemistry, hybridization techniques and biochemistry). Standard techniques are used for molecular, genetic and biochemical methods. See, generally, Sambrook et al., Molecular Cloning: A Laboratory Manual, 2d ed. (1989) Cold Spring Harbor Laboratory Press, Cold Spring Harbor, N.Y. and Ausubel et al., Short Protocols in Molecular Biology (1999) 4th Ed, John Wiley & Sons, Inc.; as well as Guthrie et al., Guide to Yeast Genetics and Molecular Biology, Methods in Enzymology, Vol. 194, Academic Press, Inc., (1991), PCR Protocols: A Guide to Methods and Applications (Innis, et al, 1990, Academic Press, San Diego, Calif.), McPherson et al., PCR Volume 1, Oxford University Press, (1991), Culture of Animal Cells: A Manual of Basic Technique, 2nd Ed (R. I. Freshney, 1987, Liss, Inc. New York, N.Y.), and Gene Transfer and Expression Protocols, pp. 109-128, ed. E. J. Murray, The Humana Press Inc., Clifton, N.J.).

3β-Amino-5α-Androstane Hydrochloride (K118)

As used herein, in one embodiment, a suitable SHIP inhibitor for use in the methods of the present invention can include, without limitation, the following SHIP inhibitor compound of Formula 28, wherein X=NH$_2$ or NH$_3$Cl, as well as any derivatives or analogs thereof:

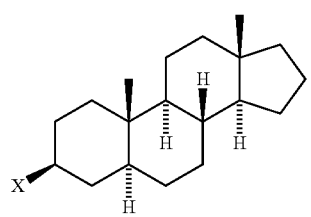

Formula 28

More particularly, the compound described herein as "K118" refers to the SHIP inhibitor compound of Formula 28 wherein X is NH$_3$Cl. K118 is also referred to herein as 3β-amino-5α-androstane hydrochloride. Aspects of K118 are further described in Example 20, Example 21, and the figures associated with the relevant Examples. For example, as described in Example 21, K118 can be effective as a SHIP inhibitor to prevent or reduce obesity without negatively impacting bone density. K118 is a water-soluble derivative of 3AC and has comparable SHIP1 inhibitor activity. Because K118 is water-soluble, it can be used for pharmacological targeting of SHIP1. K118 can also be described as being a pan-SHIP1/2 type of inhibitor.

Various analogs of K118 can include, without limitation, the compounds identified herein as Formula 11, Formula 14, Formula 17, Formula 20, Formula 23, Formula 24, Formula 25, Formula 31, Formula 32, Formula 33, Formula 34, Formula 35, Formula 36, and Formula 37, wherein X=NH$_2$ or NH$_3$Cl.

Provided below are more particular terms and aspects regarding various embodiments for the use of K118 as a therapeutic composition, although the use of K118 is not meant to be limited by the terms and aspects described below. Further, as used herein, reference to K118 is also meant to relate to the derivatives, analogs, and any variations of K118.

An "effective amount" of K118, and pharmaceutically acceptable salts or derivatives thereof, may be in a dosing range of from about 0.05 mg/kg to about 150 mg/kg and particularly in a dosing range of from about 0.1 mg/kg to about 100 mg/kg. More particularly, the dosing range can be from 0.08 mg/kg to 140 mg/kg, from 0.1 mg/kg to 130 mg/kg, from 0.1 mg/kg to 120 mg/kg, from 0.1 mg/kg to 110 mg/kg, from 0.1 mg/kg to 110 mg/kg, from 0.5 mg/kg to 100 mg/kg, from 1 mg/kg to 100 mg/kg, from 10 mg/kg to 80 mg/kg, from 20 mg/kg to 70 mg/kg, from 20 mg/kg to 60 mg/kg, from 20 mg/kg to 50 mg/kg, from 20 mg/kg to 40 mg/kg, and from 20 mg/kg to 30 mg/kg.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitory active metabolite or residue thereof.

In one embodiment of the present invention, K118 is administered at a dose from 0.05 mg/kg to 150 mg/kg or more particularly at a dose from 0.1 mg/kg to 100 mg/kg once a day, every other day, three times a week, twice a week, once a week etc. In another embodiment, K118 is administered at a dose from 0.08 mg/kg to 140 mg/kg, from 0.1 mg/kg to 130 mg/kg, from 0.1 mg/kg to 120 mg/kg, from 0.1 mg/kg to 110 mg/kg, from 0.1 mg/kg to 110 mg/kg, from 0.5 mg/kg to 100 mg/kg, from 1 mg/kg to 100 mg/kg, from 10 mg/kg to 80 mg/kg, from 20 mg/kg to 70 mg/kg, from 20 mg/kg to 60 mg/kg, from 20 mg/kg to 50 mg/kg, from 20 mg/kg to 40 mg/kg, and from 20 mg/kg to 30 mg/kg once a day, every other day, three times a week, twice a week, once a week, etc.

The term "pharmaceutically acceptable" means that a compound or combination of compounds is sufficiently compatible with the other ingredients of a formulation, and not deleterious to the patient up to those levels acceptable by the industry standards.

Therefore, K118 may be formulated into various pharmaceutical forms for administration purposes. As appropriate compositions there may be cited all compositions usually employed for systemically administering drugs. To prepare the pharmaceutical compositions of this invention, an effective amount of K118 as the active ingredient is combined in intimate admixture with a pharmaceutically acceptable carrier, which carrier may take a wide variety of forms depending on the manner of preparation desired for administration.

These pharmaceutical compositions are desirable in unitary dosage form suitable, particularly, for administration orally, rectally, intraperitoneally, transdermally, intradermally, topically, by inhalation, nasally, buccally, vaginally, via an implanted reservoir or by parenteral routes. The term "parenteral" as used herein includes subcutaneous, intravenous, intramuscular, intra-articular, intra-synovial, intrasternal, intrathecal, intrahepatic, intralesional and intracranial injection or infusion techniques.

The term "pharmaceutically acceptable carrier" refers to a non-toxic carrier, adjuvant, or vehicle that does not destroy the pharmacological activity of the compound with which it is formulated. Pharmaceutically acceptable carriers, adjuvants or vehicles that may be used in the compositions of this disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium, hydrogen, phosphate, potassium hydrogen phosphate, sodium chloride, zinc salts, colloidal silica, magnesium, trisilicate, polyvinylpyrrolidone, cellulose-based substances, polyethylene glycol, sodium carboxymethylcellulose, polyacrylates, waxes, polyethylene-polyoxypropylene-block polymers, polyethylene glycol and wool fat.

In one embodiment of the present invention, K118 is administered orally. K118 can be administered by the oral route in solid dosage forms, such as tablets, capsules, and powders, or in liquid dosage forms, such as elixirs, syrups, suspensions, pharmaceutically acceptable emulsions, microemulsions, solutions, suspensions, syrups and elixirs. The pharmaceutical compositions of this invention can also be administered parenterally, in sterile liquid dosage forms.

In preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders pills, capsules, and tablets. Liquid dosage forms may contain inert diluents commonly used in the art such as, for example, water or other solvents, solubilizing agents and emulsifiers such as ethyl alcohol, isopropyl alcohol ethyl carbonate, ethyl acetate benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents. Because of their ease in administration, tablets and capsules represent the most advantageous oral dosage unit forms, in which case solid pharmaceutical carriers are obviously employed.

K118 may as well be administered in oral dosage forms such as the ones described in U.S. Pat. No. 7,182,958, as a free drug in admixture with a diluent, a lubricant, a hydrophilic binder selected from the group consisting of a cellulose derivative, povidone, and a mixture thereof, a disintegrant selected from the group consisting of crospovidone, croscarmellose sodium, and a mixture thereof, and, optionally, microcrystalline cellulose and/or a wetting agent. Optionally, the formulation additionally comprises a second diluent.

K118 may as well be administered as a coprecipitate preparation with a polymer, as disclosed in U.S. Pat. No. 5,955,326, wherein the polymer is for example hydroxypropyl methylcellulose phthalate. This coprecipitate preparation is prepared, then milled, mixed with excipients, and compressed into tablets for oral administration.

Solid dosage forms for real administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, vinyl alcohol and glycerol monostearate, h)

absorbents such as kaolin and bentonite clay, and i) lubricants such as talc, calcium stearate, magnesium stearate, solid polyethylene glycols, sodium lauryl sulfide, and mixtures thereof. In the case of capsules, tablets and pills, the dosage form may also comprise buffering agents.

In preliminary studies, K118 was shown to induce increases in immunoregulatory cells when delivered orally at 10 mg/kg. A significant increase was observed in the frequency of myeloid derived suppressor cells (MDSC) expressing both Gr1 and Mac1 cell markers. This was observed in the spleen of treated mice. Significant increases were also observed in the frequency of "natural" T regulatory cells (nTreg), characterized by expression of $CD4^+$ $CD25^+FoxP3^+$, in both the spleen and in the mesenteric lymph node (mLN). Finally, it was observed a trend for increased neutrophil numbers, as is observed with intraperitoneal injection of SHIP1 inhibitor 3AC. K118 was administered in water, and in wt C57BL/76 mice.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

Provided compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Also, in certain embodiments, free K118 drug is preferred in particulate form, and wherein at least 90% of the particles have a particle size of less than about 40 microns, and preferably less than 30 microns. Highly preferred particulate forms of the compound (I) have at least 90% of the particles less than 25 microns in size. Most preferred forms of the free compound (I) are those wherein 90% of the particles are less than 10 microns in size, as described and prepared in U.S. Pat. No. 6,821,975.

Formulations for parenteral administration may be in the form of aqueous or non-aqueous isotonic sterile injection solutions or suspensions. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. These latter suitable additives may be anti-oxidants, preservatives, stabilizing agents, emulsifiers, salts for influencing the osmotic pressure, and/or buffer substances.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a provided compound, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled.

Examples of other biodegradable polymers include poly (orthoesters) and poly(anhydrides). Depot injectable formulations are also prepared by entrapping the compound in liposomes or microemulsions that are compatible with body tissues.

In one embodiment of the present invention, K118 is administered transdermally. In one embodiment of the present invention, K118 is administered topically.

As appropriate topical or transdermal compositions there may be cited for example gels, jellies, creams, pastes, emulsions, dispersions, ointments, films, sponges, foams, aerosols, powders, implants, patches. In the compositions suitable for topical cutaneous administration, the carrier optionally comprises a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a cream or gel.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Pharmaceutically acceptable compositions provided herein may also be administered by nasal aerosol or inhalation. Such compositions are prepared according to techniques well-known in the art of pharmaceutical formulation and may be prepared as solutions in saline, employing benzyl alcohol or other suitable preservatives, absorption promotors to enhance bioavailability, fluorocarbons, and/or other conventional solubilizing or dispersing agents.

Pharmaceutically acceptable compositions provided herein may be formulated for oral administration. Such formulations may be administered with or without food. In some embodiments, pharmaceutically acceptable compositions of this disclosure are administered without food. In other embodiments, pharmaceutically acceptable compositions of this disclosure are administered with food.

The amount of provided compounds that may be combined with carrier materials to produce a composition in a single dosage form will vary depending upon the patient to be treated and the particular mode of administration. Provided compositions may be formulate such that a dosage of between 0.01-150 mg/kg body weight/day of the inhibitor can be administered to a patient receiving these compositions.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

Notwithstanding the effective amounts and doses indicated above, still the dose of K118, its pharmaceutically acceptable salts and solvates thereof to be administered will depend on the individual case and, as customary, is to be adapted to the conditions of the individual case for an optimum effect. Thus it depends, of course, on the frequency of administration and on the potency and duration of action of the compound employed in each case for therapy or prophylaxis, but also on the nature and severity of the disease and symptoms, and on the sex, age, weight co-medication and individual responsiveness of the subject to be treated and on whether the therapy is acute or prophylactic. Doses may be adapted in function of weight and for paediatric applications. Daily doses may be administered q.d. or in multiple quantities such as b.i.d., t.i.d. or q.i.d. Alternatively, doses may be administered every other day, every three, every four, every five, every six, every seven days, every other week, every month.

In one embodiment of the method of the present invention, the SHIP1 or pan-SHIP1/2 inhibitor is injected intraperitoneally at between about 10 mg/kg and 80 mg/kg of body weight.

In another embodiment of the method of the present invention, the SHIP1 inhibitor or the pan-SHIP1/2 inhibitor is administered periodically at least once per day or continuously to the subject during an administration period having a duration of no more than seven days. In one embodiment, the administration period has a duration of three days or less. In another embodiment, the administration period is immediately followed by a rest period during which no SHIP1 inhibitor or pan-SHIP1/2 inhibitor is administered, wherein a cycle of one administration period followed by one rest period is repeated. In another embodiment, the administration period has a duration of three days or less and the rest period has a duration of between two and ten days, inclusive.

In one embodiment of the method of the present invention, the subject suffers from a bacterial, viral, or parasitic infection, or from cancer.

In one aspect, the present disclosure provides a pharmaceutical composition composing a SHIP inhibitor compound, including, without limitation, a SHIP1 inhibitor and/or a pan-SHIP1/2 inhibitor compound as described herein, or a pharmaceutically acceptable salt thereof.

EXAMPLES

The following examples are intended to illustrate particular embodiments of the present invention, but are by no means intended to limit the scope of the present invention.

Example 1

Small Molecule Inhibition of SHIP1 Induces Broad Activation of Natural Killer Cells Small molecule inhibition of SHIP1 provides, for the first time, an inexpensive mechanism to activate NK cells. This technology could be used in the treatment of bacterial, viral and parasitic infections and well in the treatment of several different types of cancer.

Mice with NK cell conditional deletion of SHIP1 have NK cells that are hyporesponsive when stimulated ex vivo with NK1.1, NKp46 or NKG2D antibodies however it is presently unclear why this occurs. These NK cells have increased phosphorylation of activation markers including Akt, mTOR (FIG. 3) as well as increased expression of NK cell education and development markers such as KLRG1 and DNAM1. We hypothesized that short term or periodic inhibition of SHIP1 would result in NK cell hyperresponsiveness while chronic SHIP1 deficiency would lead to hyporesponsive NK cells.

Short-term (2 day) treatment (or treatments) of mice with the small-molecule SHIP1 inhibitor 3 α-aminocholestane (3AC) results in significantly increased IFNγ production compared to NK cells harvested from vehicle treated mice following ex vivo NK cell activation (FIG. 1). Harvested NK cells were activated by crosslinking activating receptors including NK1.1, NKp46 and NKG2D with plate bound antibody. All receptors used to activate NK cells resulted in increased IFNγ production by NK cells from 3AC treated mice indicating that the NK cells are broadly hyperresponsive. NK cells are important for host defense against bacterial and parasitic infection and against virally infected and malignantly transformed cells. In several different types of cancer NK cells are present in the tumor but are unable to respond due to NK cell exhaustion. Thus, small molecule inhibition of SHIP1 provides a mechanism to increase NK cell activation for the treatment of a wide range of human diseases. Further, several different types of cancer cells undergo apoptosis when treated with small molecule SHIP1 inhibitors providing two independent mechanisms to target malignancy and thus potentially increasing the efficacy of this treatment.

Figure 3:
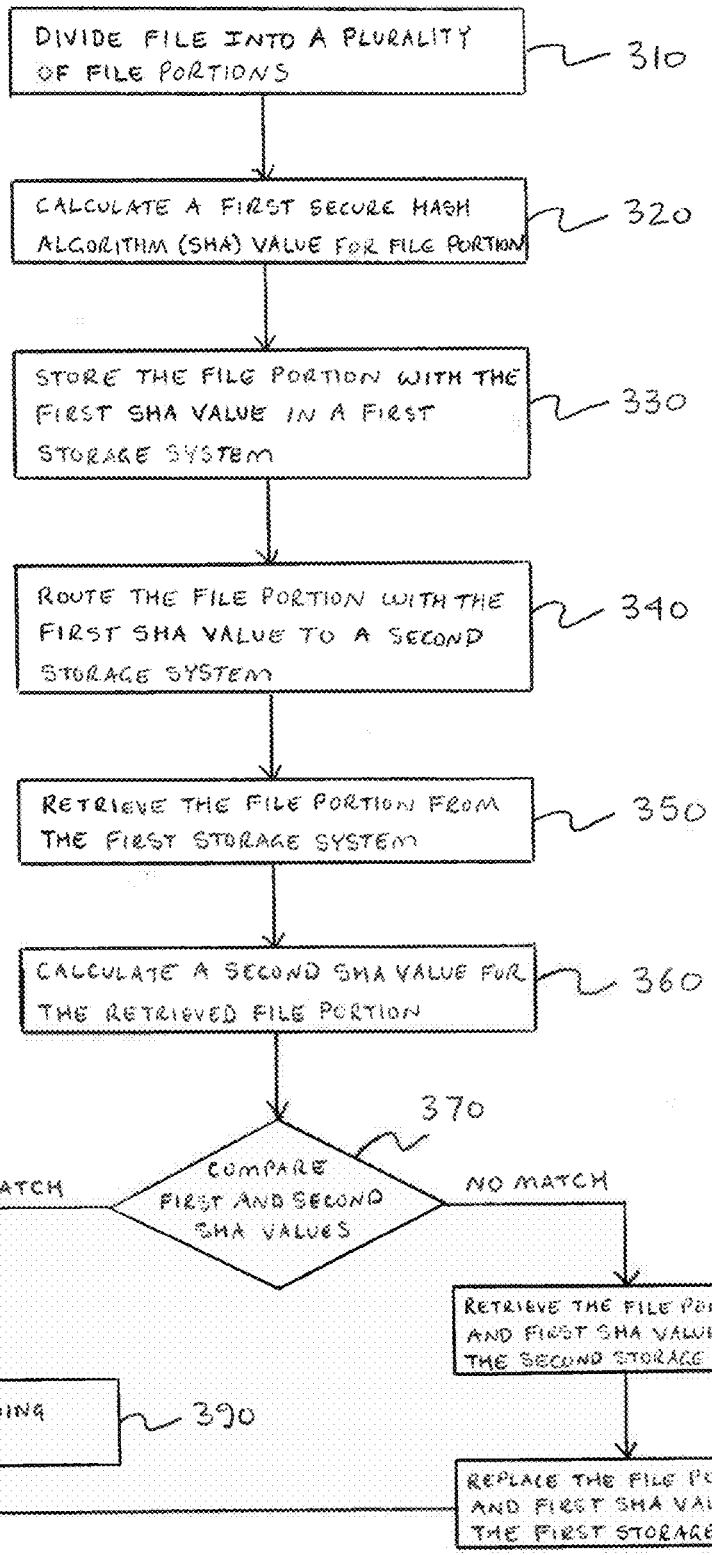
FIGS. 3A-3B: SHIP1 deficient NK cells have increased phosphorylation of activating signaling pathways. Splenocytes harvested from NCR1Cre$^+$SHIP1$^{flox/flox}$ mice and SHIP1$^{flox/flox}$ controls were stained with anti-NK1.1, anti-CD3ε and a viability dye. Following fixation and permeabilization cells were stained with (A) anti-pS473 Akt (FIG. 3A), (B) anti-pS2448 mTOR (FIG. 3B) antibodies and analyzed by flow cytometry. Graphs are expressed as the median fluorescence intensity (MFI) of the given signaling molecule or transcription factor after backgating on singlets, live cells, lymphocytes and NK1.1$^+$ CD3ε$^-$Nk cells. 4 NCR1Cre$^+$SHIP1$^{flox/flox}$ mice and 4 SHIP1$^{flox/flox}$ controls.

Levels of Akt/mTOR Signaling in SHIP1 Deficient Cells:

NK cells from mice with NK conditional deletion of SHIP1, NCR1CreSHIP$^{flox/flox}$ NK cells, produce significantly decreased levels of IFNγ after ex vivo crosslinking of the activating receptors NK1.1, NLp46 or NKG2D with platebound antibody. Due to this hyporesponsiveness we hypothesized that intracellular signaling molecules involved in NK cell survival, proliferation and activation would be decreased. Surprisingly NK cells from NCR1CreSHIP$^{flox/flox}$ mice had significantly increased levels of phosphorylated Akt and mTOR (FIG. 3). The Akt/mTOR signaling pathway promotes NK cell activation and survival. Thus in the absence of SHIP1 signaling phenotype is consistent with an activated NK cell.

IFNγ Production Assay:

Mice treated with mice with a small-molecule SHIP1 inhibitor 3 α-aminocholestane (3AC, also referred to as SHIPi or a SHIP inhibitor) produced significantly increased amounts of IFNγ following ex vivo stimulation with either anti-NK1.1, anti-NKp46 or anti-NKG2D antibodies (FIG. 1). This indicates that SHIPi broadly decreases the NK threshold for activation as NK cells from SHIPi treated mice produce supernormal levels of IFNγ after activation from three distinct NK cell receptors (FIG. 1).

IFNγ production assay methods: Mice were treated daily with SHIPi (33 mg/kg) for two days. Mice were sacrificed by CO$_2$ toxicity on the third day. Splenocytes were harvested and incubated for four-five hours in six well plates in the presence of Golgiplug (BD) either alone, in plates coated with either anti-NK1.1 (PK136), anti-NKp46 (2PA1.4) or anti-NKG2D (A10) antibody or in uncoated plates but with PMA (phorbol myristic acid) and ionomycin as a positive control. After incubation splenocytes were removed from the plates, Fc Receptors were blocked (2.4G2) and cells were stained with the Invitrogen Aqua Live/Dead cell exclusion dye. NK cells were identified by staining for either NK1.1 (PK136) or NKp46 (29A1.4) and CD3ε+ (145-2C11). T cells were excluded. Cells were fixed and permeabilized (BD Cytofx/Cytoperm kit), intracellular Fc receptors were blocked (2.4G2) and stained for IFNγ (XMG1.2). Samples were run on a BD Fortessa flow cytometer and analyzed using FloJo software.

Example 2

In Vivo Tests of Effect of Short Term SHIPi on NK Cells

Figure 2:
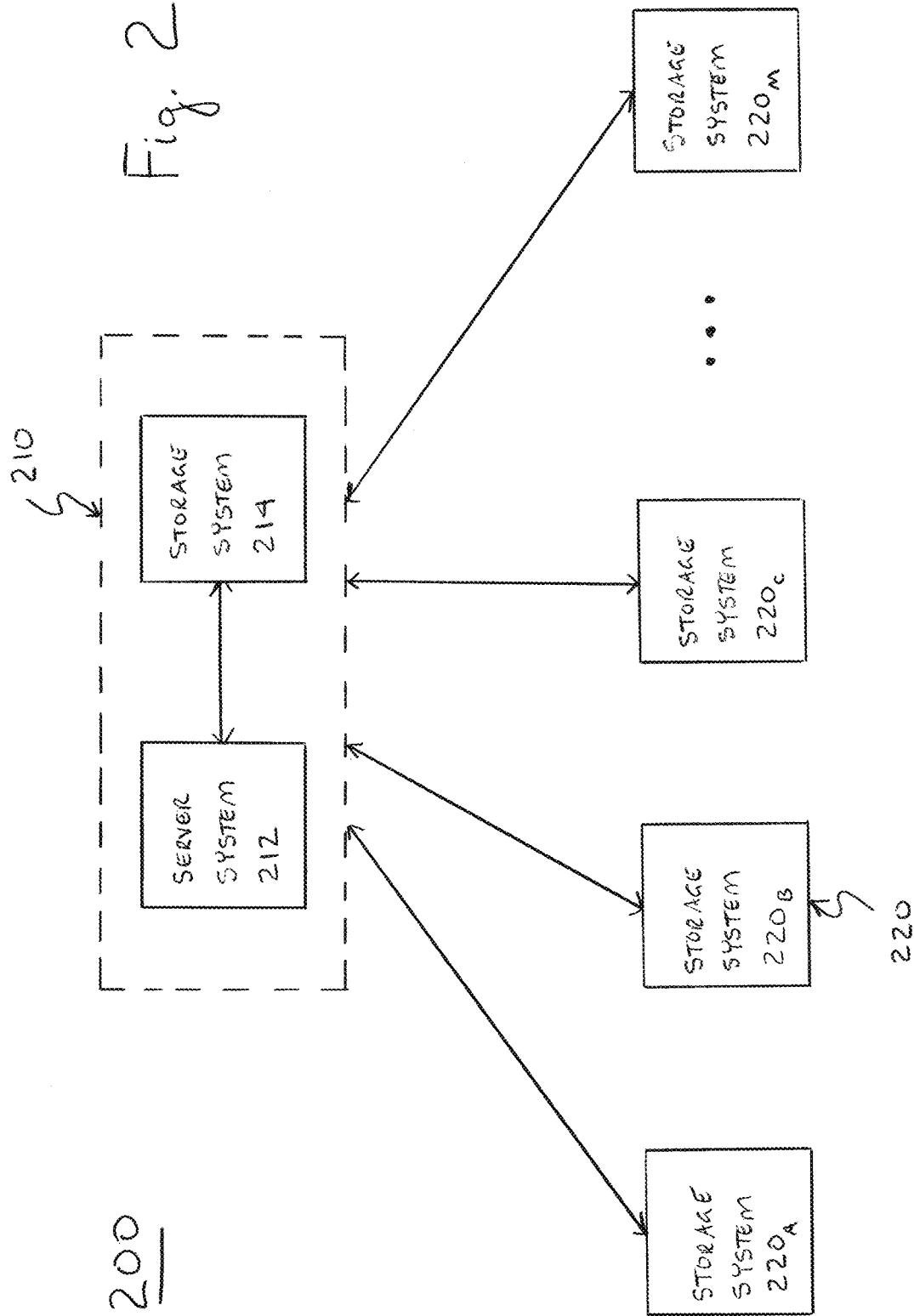
FIG. 2: C57BL/6 mice received either RM A cells (3AC RMA and Veh RMA groups) or RMA cells transfected with the NKG2D ligand Rae1 (3AC Rae1 and Veh Rae1 groups) and were treated two consecutive days each week starting twelve hours after receiving the tumor. SHIPi treated mice bearing RMA-Rae1 tumors (3AC Rae1 group) had significantly increased survival compared to all other groups of mice. The Kaplan-Meyer survival curve represents two independent, pooled, experiments of RMA-Rae1 tumor bearing mice treated with either vehicle (n=10/experiment) or SHIPi (n=10/experiment) or one experiment of RMA tumor bearing mice treated with either vehicle (n=10/experiment) or SHIPi (n=10/experiment).
Figure 4:
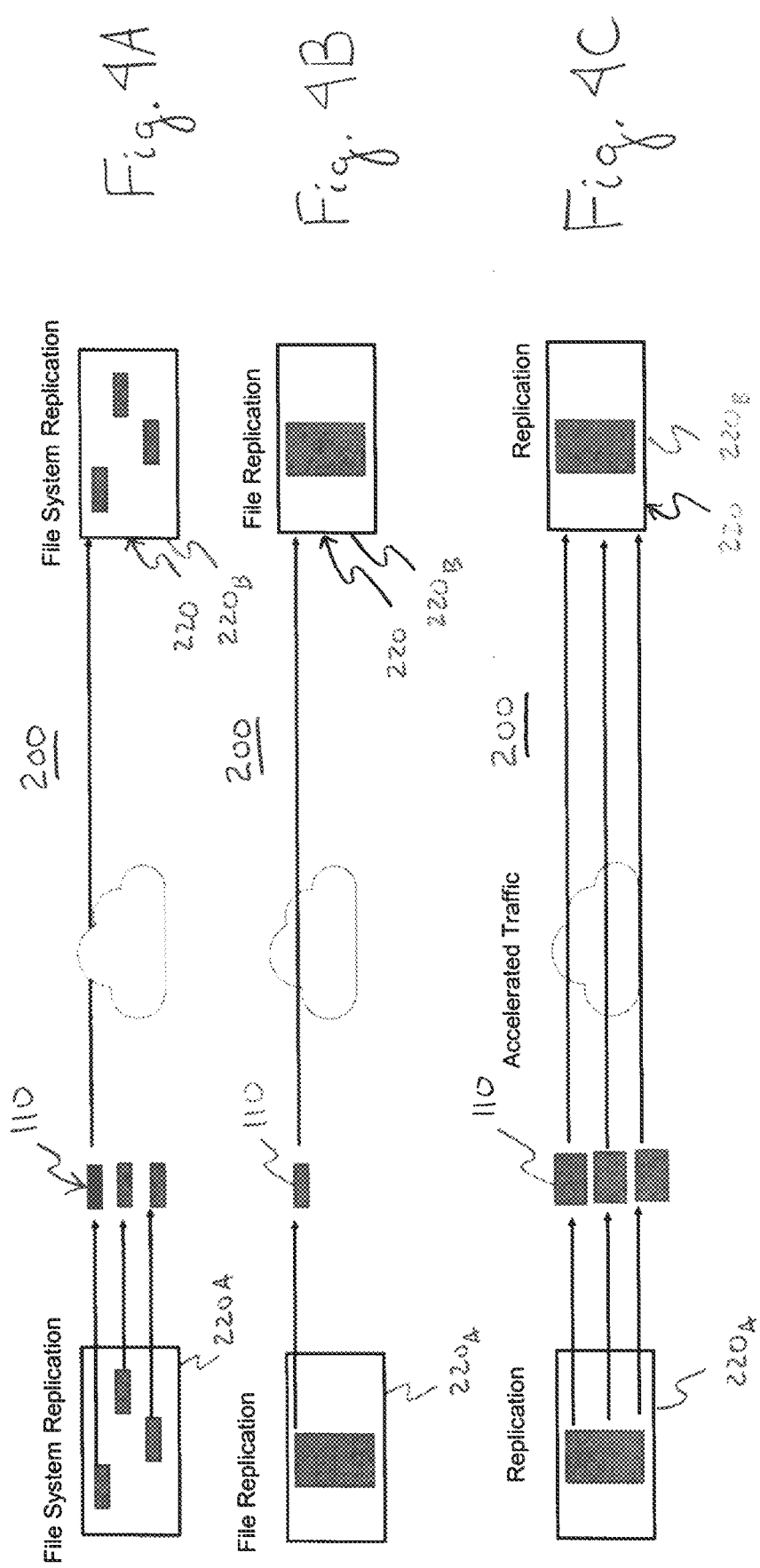
FIG. 4A-4B: SHIPi treated mice have increased tumor rejection.
Figure 5:
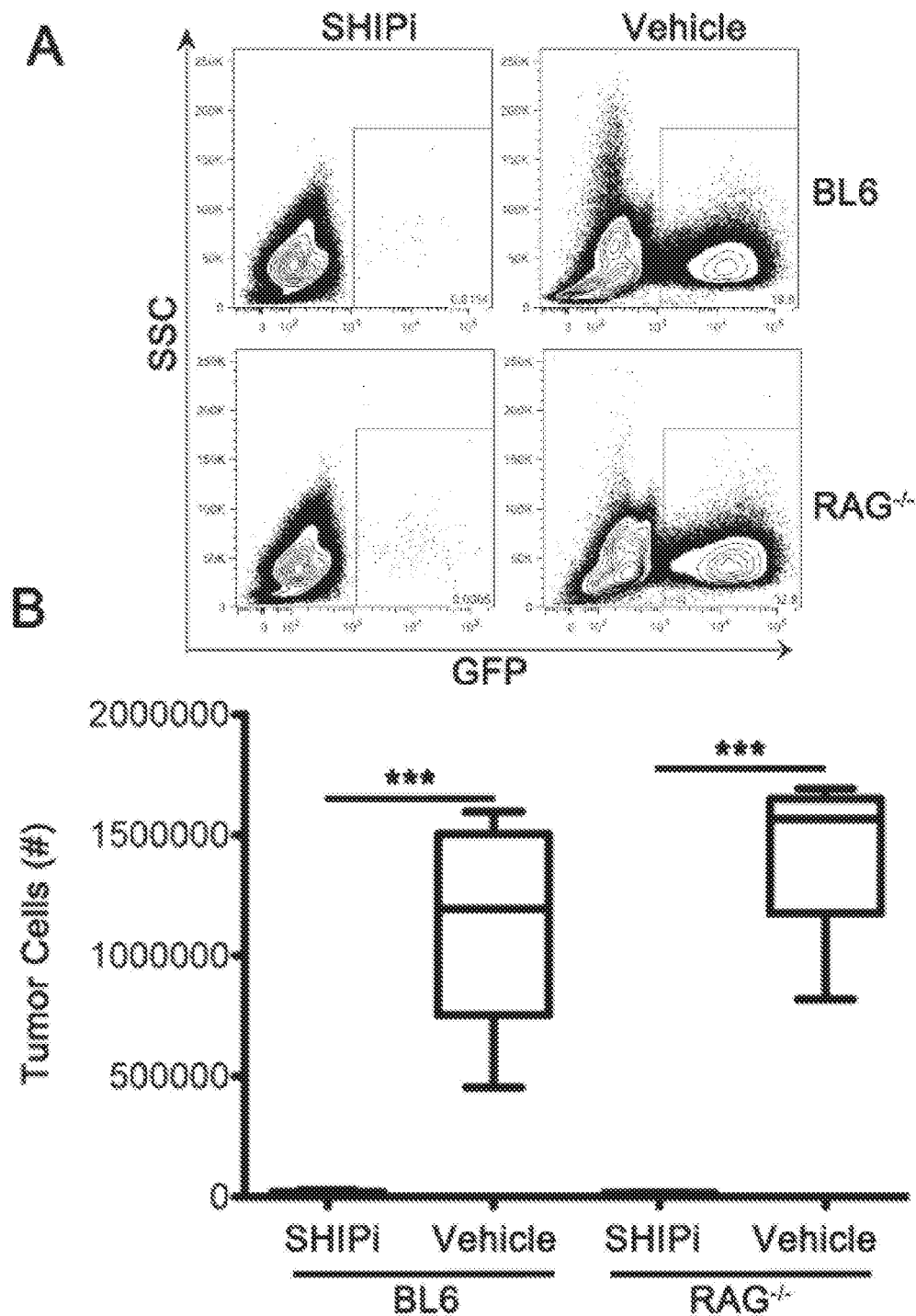
FIGS. 5A-5B: SHIPi mediated tumor rejection is not due to B or T cells.
Figure 6:
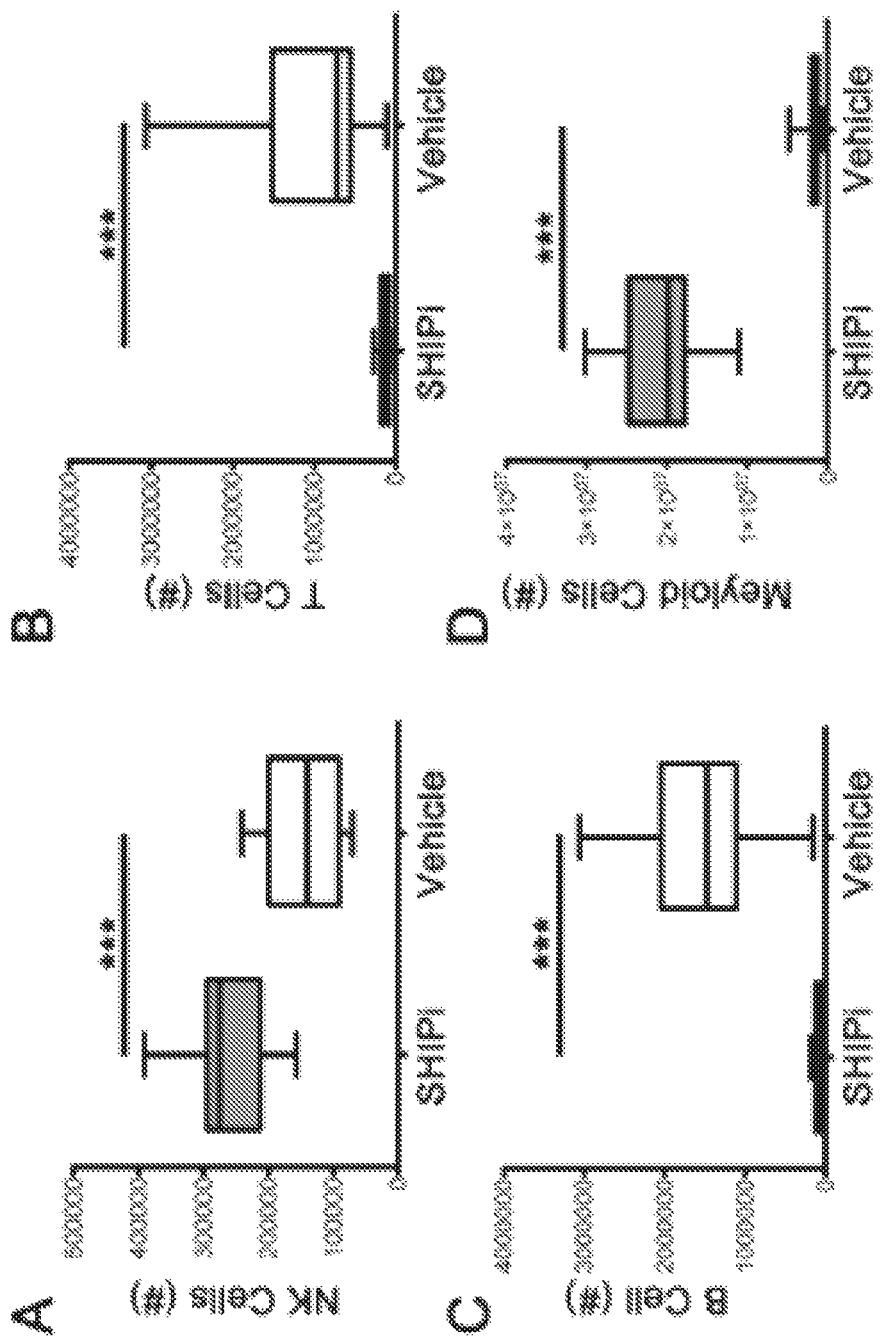
FIGS. 6A-6D: SHIPi treated mice have increased peritoneal myeloid and NK cells.
Figure 7:
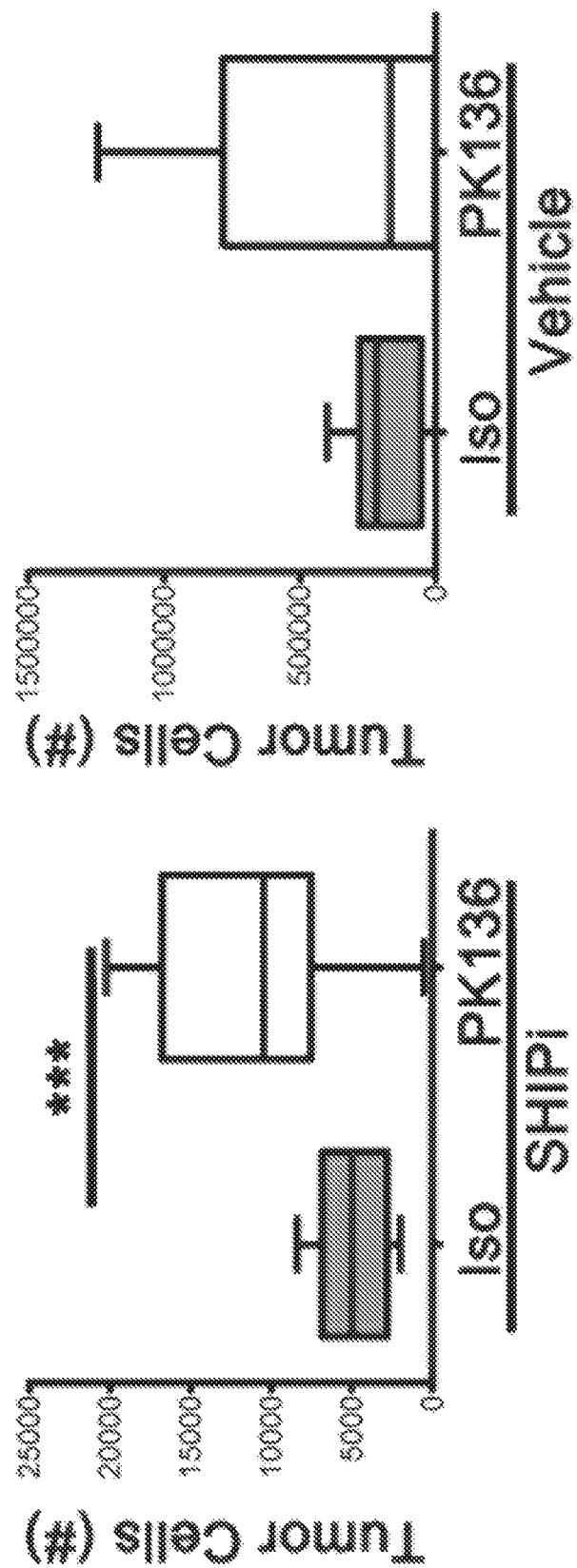
FIG. 7: Graphs showing the impact of acute SHIPi treatment is reduced by in vivo depletion of NK cells.

To determine if short term administration of SHIPi could have an in vivo functional effect we injected 5×10$^5$ RMA cells transected with the NKG2D ligand Rae1 into C57BL/6 mice. RMA is a mouse BL/6 derived T cell lymphoma cell line (raucher virus induced cell leukemia cell line); thus a rejection of a tumor graft in BL/6 mice is due to the presence of the Rae1 ligand or due to SHIPi treatment. Mice were treated with SHIPi (33 mg/kg) for two consecutive days and on the third day peritoneal lavage was performed to recover peritoneal contents. As seen in FIG. 4, mice treated with SHIPi had significantly reduced tumor burden compared to vehicle treated controls. This effect is not due to a non-NK cell lymphocyte as RAKG$^{-/-}$ mice retained protection (FIG. 5). Furthermore, this effect is at least partially due to NK cells as when mice were pretreated with anti-NK1.1 antibody (PK136; 200 ug 24 hours before tumor injection) which results in depletion of NK cells, protection is significantly reduced compared to mice pretreated with an isotype control antibody (and thus have normal numbers of NK cells) (FIG. 7). Tumor bearing mice that received SHIPi had significantly increased numbers of NK cells present in the peritoneal cavity after two days of SHIPi treatment which could aid in the therapeutic effect (FIG. 6). Finally, showing that there is a survival benefit for mice receiving short term SHIPi, C57BL/6 mice were injected with 1×10$^5$ RMA or RMA cells transected with the NKG2D ligand Rae1 and then were treated two consecutive days with SHIPi or with vehicle control. This was repeated each week such that mice received treatment or vehicle twice a week with five days rest in between each treatment. Treatment start days were spaced a week apart. There was no significant survival difference between SHIPi, vehicle treated mice that received RMA cells and vehicle treated mice that received RMA-Rae1 cell (FIG. 2). However, SHIPi treated mice had significantly increased survival compared to each of the other three groups of mice (FIG. 2).

Example 3

Treating of Patients Using SHIPi to Increase Patient's NK Cell Activation

An effective dose of SHIP inhibitor (e.g. 3AC, K118) is administered by any appropriate means (e.g., orally, IV, IP) to a patient for short administration periods separated by rest periods during which no SHIP inhibitor is administered. This cycle of SHIPi administration and rest periods can be repeated multiple times (e.g., 2, 3, 4, 5, 7, 10, etc). The short administration periods can be 1, 2, 3 or more days, with the SHIPi administered approximately daily or more than daily (e.g. twice or thrice a day). The rest periods can be longer or shorter than the administration periods, and can be 2, 3, 4, 5, 6, 7, 8, 9, 10, 12, 15 or longer. One administration protocol is to administer SHIPi daily for 2 days followed by a 5-day rest period, with the cycle repeated multiple times. This treatment can likely be used in conjunction with an antibody therapy as NK cells are thought to assist in killing via antibodies such as Rituximab and Herceptin via a process known as antibody dependent cell mediated cytotoxicity.

Citation of a reference herein shall not be construed as an admission that such reference as prior art to the present invention. All references cited herein are hereby incorporated by reference in their entirety.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A method of activating natural killer (NK) cells in a subject suffering from an illness or condition for which NK cells provide a host defense, said method comprising:
   periodically administering a safe and effective amount of a SHIP1 inhibitor to the subject, wherein an administration period is immediately followed by a rest period during which no SHIP1 inhibitor is administered, wherein a cycle of one administration period followed by one rest period is repeated, wherein the administration period has a duration of no less than two days, but no more than three days, and the rest period has a duration of between two and ten days, inclusive, and wherein periodic administration of the SHIP1 inhibitor activates NK cells in the subject.

2. The method according to claim 1, wherein the SHIP I inhibitor is a SHIP inhibitor compound of formula (I), or a pharmaceutically acceptable salt thereof, wherein formula (I) is as follows:

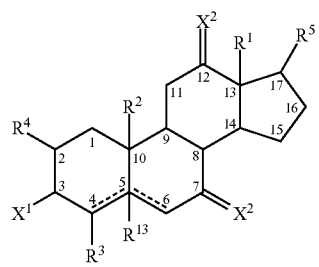

wherein
   ---- at the 4,5 and 5,6 positions represents a single or double bond, with the proviso that the sum of double bonds present at the 4,5 and 5,6 positions is 0 or 1;
   $R^1$ is a straight chain C1-C4 alkyl or C1-C4 haloalkyl;
   $R^2$ is hydrogen, methyl, or halomethyl;
   $R^3$ and $R^{13}$ (when present), are individually selected from hydrogen, substituted or unsubstituted amino, $C_1$-$C_4$ alkyl, $C_1$-$C_4$ haloalkyl, and alkenyl;
   $R^4$ is hydrogen, hydroxy, substituted or unsubstituted amino, C1-C4 alkyl, or benzyl;
   $R^5$ represents hydrogen or an alkyl group;
   $X^1$ is selected from the group consisting of hydrogen, hydroxy, mercapto, alkoxy, aryloxy, alkylthio, arylthio, alkylcarbonamido, alkoxycarbonamido, arylcarbonamido, aryloxycarbonamido, alkylsulfonamido, arylsulfonamido, substituted or unsubstituted amino, and aminoalkyl; and
   each $X^2$ individually represents a divalent oxo atom or two hydrogen atoms;
   with the proviso that $X^1$ cannot be a primary amino group when: $R^1$ and $R^2$ are each methyl; $X^2$, $R^3$, $R^4$, and $R^{13}$ are each hydrogen; and $R^5$ represents a 1,5-dimethylhexyl alkyl group.

3. The method according to claim 2, wherein at least one of $X^1$, $R^3$, and $R^4$ is substituted or unsubstituted amino.

4. The method according to claim 3, wherein the substituted or unsubstituted amino is $NH_2$ or $NH_3Cl$.

5. The method according to claim 2, wherein $X^1$ is $NH_2$ or $NH_3Cl$.

6. The method according to claim 2, wherein said compound of formula (I) is a compound of a formula selected from the group consisting of:

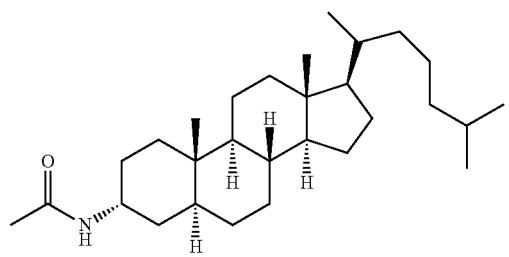

Formula 10

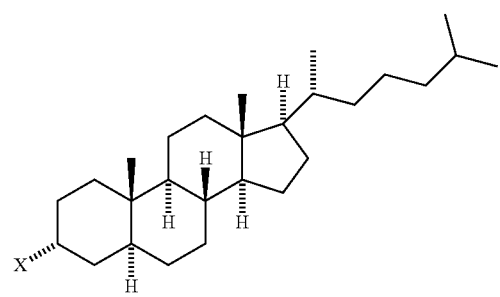

Formula 11

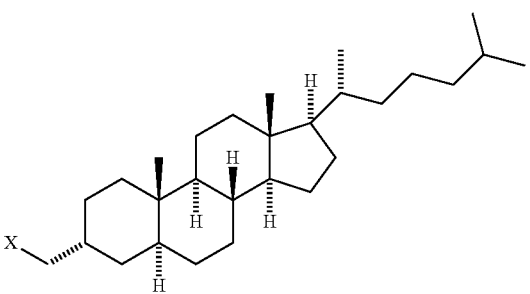

Formula 12

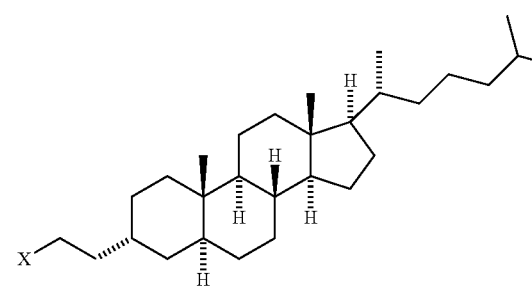

Formula 13

Formula 14
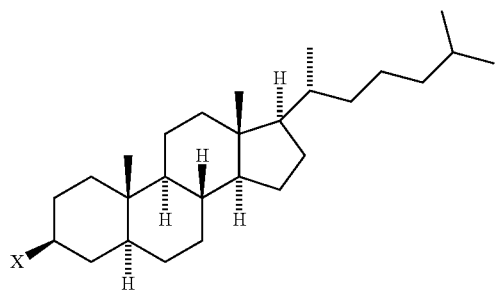
,
Formula 15
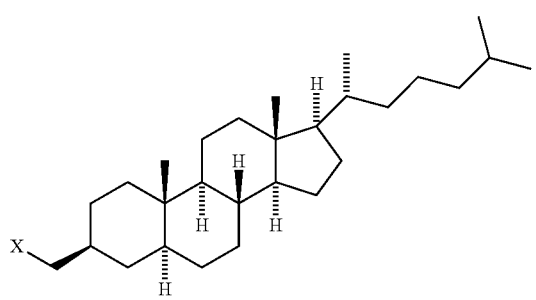
,
Formula 16
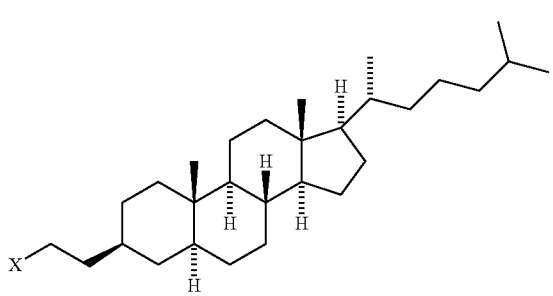
,
Formula 17
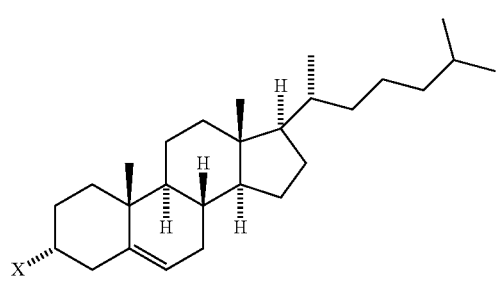
,
Formula 18
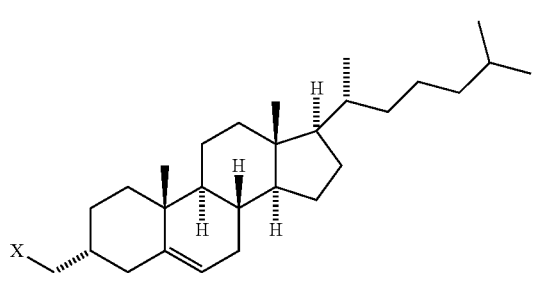
,
Formula 19
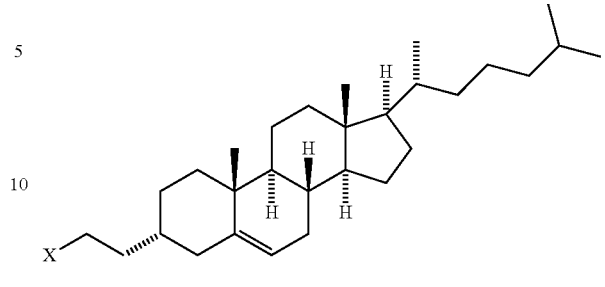
,
Formula 20
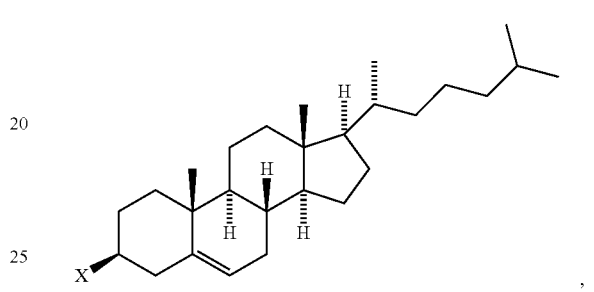
,
Formula 21
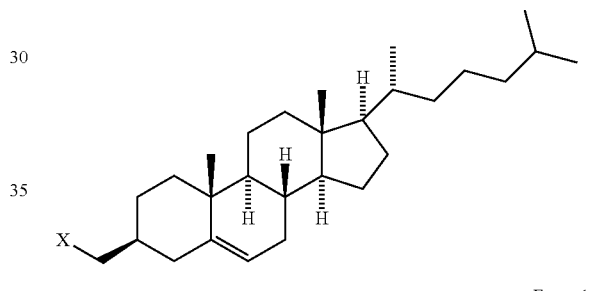
,
Formula 22
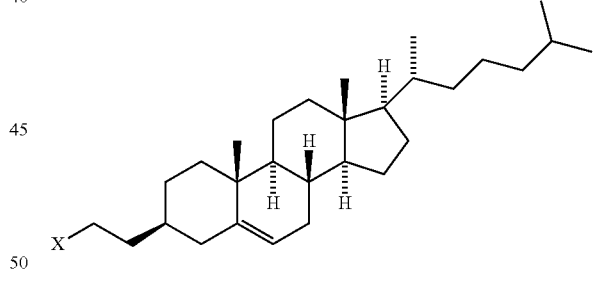
,
Formula 25
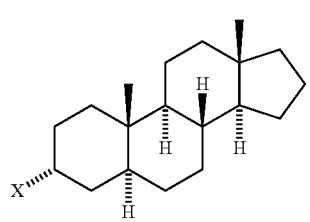
, Formula 26
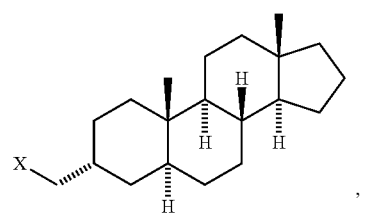

Formula 27
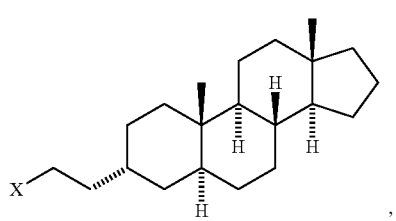

Formula 28
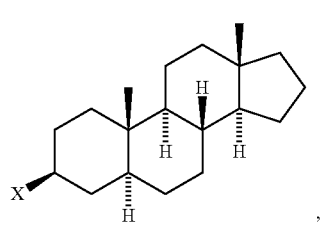

Formula 29
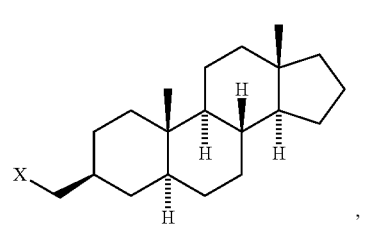

Formula 30
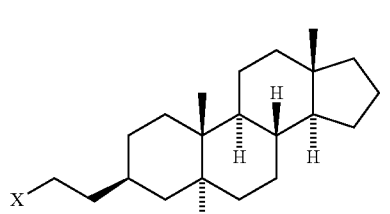

Formula 31
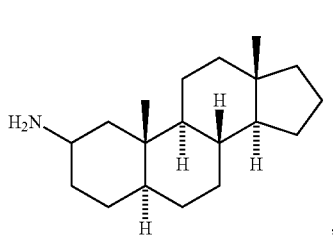

Formula 32
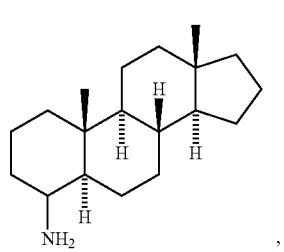

Formula 33
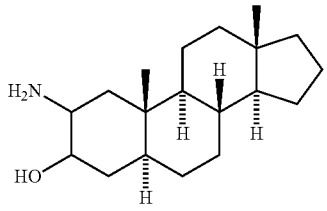

Formula 34
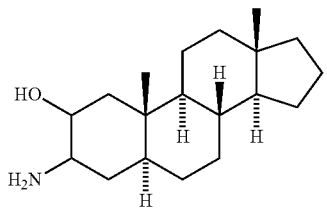

Formula 35
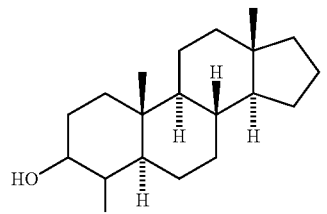

Formula 36
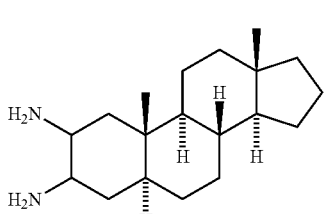

Formula 37
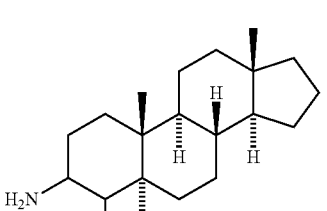

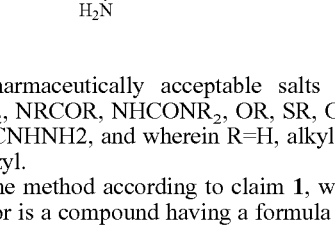

and pharmaceutically acceptable salts thereof, wherein X=NR$_2$, NRCOR, NHCONR$_2$, OR, SR, OCOR, OCONR$_2$, or NHCNHNH2, and wherein R=H, alkyl, cycloalkyl, aryl, or benzyl.

7. The method according to claim 1, wherein the SHIP1 inhibitor is a compound having a formula selected from the group consisting of:

K111
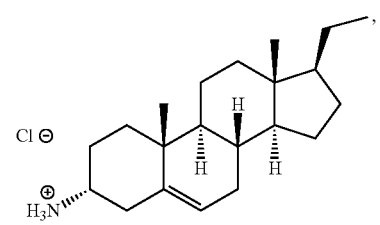

-continued

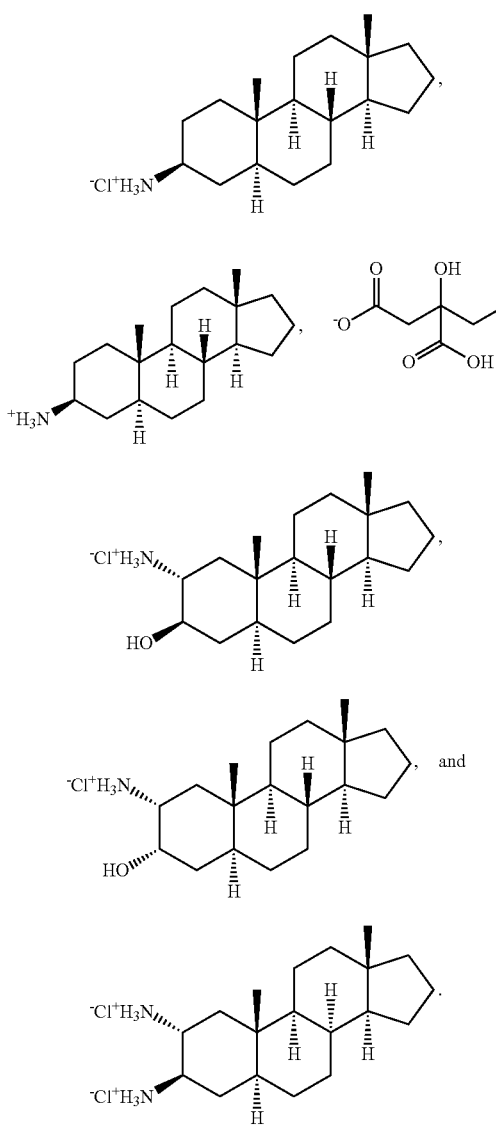

8. The method according to claim 1, wherein the SHIP1 inhibitor is administered orally, rectally, intraperitoneally, transdermally, intradermally, topically, by inhalation, nasally, buccally, vaginally, via an implanted reservoir or by parenteral routes.

9. The method according to claim 8, wherein the SHIP1 inhibitor is injected intraperitoneally at between about 10 mg/kg and 80 mg/kg of body weight.

10. The method according to claim 1, wherein said SHIP1 inhibitor is administered periodically at least once per day or continuously to the subject during an administration period having a duration of no more than seven days.

11. The method according to claim 10, wherein the administration period has a duration of three days or less.

12. The method according to claim 10, wherein the administration period is immediately followed by a rest period during which no SHIP1 inhibitor is administered, wherein a cycle of one administration period followed by one rest period is repeated.

13. The method according to claim 12, wherein the administration period has a duration of three days or less and the rest period has a duration of between two and ten days, inclusive.

14. The method according to claim 1, wherein the subject suffers from a bacterial, viral, or parasitic infection, or from cancer.

15. The method according to claim 1, wherein the SHIP I inhibitor is either a small interfering RNA (siRNA) or a microRNA (miRNA) effective to inhibit SHIP1 via RNA interference (RNAi) (post transcriptional gene silencing).

16. The method according to claim 1, wherein the SHIP inhibitor is administered orally at a concentration of 10 mg/kg.

17. The method according to claim 12, wherein the rest period is 2 days or longer.

18. The method according to claim 12, wherein the rest period is 5 days or longer.

* * * * *